(12) United States Patent
Horikawa et al.

(10) Patent No.: US 8,764,682 B2
(45) Date of Patent: Jul. 1, 2014

(54) MEASUREMENT DEVICE AND PUNCTURE DEVICE

(75) Inventors: Kiyohiro Horikawa, Ehime (JP); Takeshi Nishida, Fukuoka (JP); Yoshinori Amano, Ehime (JP); Tetsuya Takashima, Ehime (JP); Keisuke Matsumura, Ehime (JP); Masahiro Kitagawa, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 550 days.

(21) Appl. No.: 13/147,255

(22) PCT Filed: Feb. 3, 2010

(86) PCT No.: PCT/JP2010/000657
§ 371 (c)(1),
(2), (4) Date: Aug. 1, 2011

(87) PCT Pub. No.: WO2010/090015
PCT Pub. Date: Aug. 12, 2010

(65) Prior Publication Data
US 2011/0288439 A1    Nov. 24, 2011

(30) Foreign Application Priority Data

Feb. 4, 2009    (JP) .................................. 2009-023460

(51) Int. Cl.
*A61B 5/00* (2006.01)
(52) U.S. Cl.
USPC .......................................................... 600/583
(58) Field of Classification Search
CPC . A61B 5/15134; A61B 5/1411; A61B 5/6826
USPC .................. 600/573, 583, 584; 606/181–183
See application file for complete search history.

(56) References Cited

U.S. PATENT DOCUMENTS

| | | | |
|---|---|---|---|
| 5,177,751 A | | 1/1993 | Kobayashi et al. |
| 5,993,439 A * | | 11/1999 | Costello et al. ................... 606/9 |
| 6,989,633 B2 | | 1/2006 | Kunert et al. |
| 7,524,317 B2 * | | 4/2009 | Gruzdev et al. ................... 606/9 |
| 8,204,568 B2 * | | 6/2012 | Matsumoto et al. .......... 600/347 |
| 8,394,085 B2 * | | 3/2013 | Horikawa et al. ............... 606/17 |
| 8,414,504 B2 * | | 4/2013 | Fujiwara et al. .............. 600/583 |
| 2010/0030037 A1 | | 2/2010 | Matsumoto et al. |

FOREIGN PATENT DOCUMENTS

| | | |
|---|---|---|
| JP | 58-7369 | 1/1983 |
| JP | 3-235384 | 10/1991 |
| JP | 4-8459 | 1/1992 |
| JP | 6-26273 | 4/1994 |
| JP | 2003/226547 | 8/2003 |
| WO | 2008/087982 | 7/2008 |

* cited by examiner

*Primary Examiner* — Max Hindenburg
(74) *Attorney, Agent, or Firm* — Greenblum & Bernstein P.L.C.

(57) ABSTRACT

Disclosed are a measurement device and a puncture device that prevent thermal loss and enable decreased cost in laser units. A laser unit (200) of a measurement device (100) is equipped with a lens barrel (210), a laser rod (220) disposed inside the lens barrel (210), a flash lamp (230) which is disposed opposite the laser rod (220) inside the lens barrel (210) and in which an inert gas is sealed inside a hard glass tube (231), and supports (241, 242, 243, 244), which are made from a material with thermal conductivity of 100 W/(mK) or more, at least parts of which are disposed outside of the lens barrel (210), and which support the circumferential surface of the hard glass tube (231) in a housing.

22 Claims, 19 Drawing Sheets

MEASUREMENT DEVICE AND PUNCTURE DEVICE

TECHNICAL FIELD

The present invention relates to a measurement device equipped with a puncturing function of a laser puncturing method and a puncturing device.

BACKGROUND ART

A measurement device using a laser unit as a puncturing function is known.

Patent Literature 1 describes a blood glucose level measurement device including a laser unit provided inside a main body case and a laser unit including a laser rod and a flash lamp arranged to oppose each other inside a lens-barrel. The flash lamp is configured by an inert gas being sealed inside a glass tube. The flash lamp uses a quartz tube as the glass tube. The quartz tube is supported on the laser unit case by heat-resisting rubber.

CITATION LIST

Patent Literature

PTL 1
WO 2008/087982

SUMMARY OF INVENTION

Technical Problem

However, the flash lamp of a conventional laser unit is heated to a high temperature due to light emission and, in consideration of heat resistance, there has been no choice but to use a quartz tube as a glass tube. The quartz tube is very expensive and there is a disadvantage that a laser unit and a measurement device using the laser unit become expensive.

An object of the present invention is to provide a measurement device and a puncturing device capable of preventing heat damage of a laser unit and reducing the cost thereof.

Solution to Problem

The measurement device according to the present invention is a measurement device equipped with a laser unit for puncturing and the laser unit adopts a configuration including a lens-barrel, a laser rod arranged inside the lens-barrel, a flash lamp arranged to oppose the laser rod inside the lens-barrel and having an inert gas sealed inside a hard glass tube, and a support member at least a portion of which is arranged outside the lens-barrel and which supports an outer circumferential surface of the hard glass tube on the unit case and is made of a material having a thermal conductivity of 100 W/(m·K) or higher.

The puncturing device according to the present invention is a puncturing device that punctures a skin by radiating the skin with laser light generated by a laser unit and the laser unit adopts a configuration including a lens-barrel, a laser rod arranged inside the lens-barrel, a flash lamp arranged to oppose the laser rod inside the lens-barrel and having an inert gas sealed inside a hard glass tube, and a support member at least a portion of which is arranged outside the lens-barrel and which supports an outer circumferential surface of the hard glass tube on the unit case and is made of a material having a thermal conductivity of 100 W/(m·K) or higher.

Advantageous Effects of Invention

According to the present invention, thermal damage of a laser unit can be prevented by dissipating heat through support members made of a material having a thermal conductivity of 100 W/(m·K) or higher and thus, a hard glass tube can be used as a flash lamp of the laser unit. The hard glass tube is far cheaper than the quartz glass tube so that a significant cost reduction of the measurement device and puncturing device using such a laser unit can be realized.

DESCRIPTION OF EMBODIMENTS

Embodiments of the present invention will be described in detail below with reference to the drawings.

Embodiment 1

The present embodiment is a measurement device and a puncturing device characterized by a laser unit. First, a measurement device to which a laser unit is applied will be described. The laser unit can also be applied to a puncturing device similarly.

Figure 1:
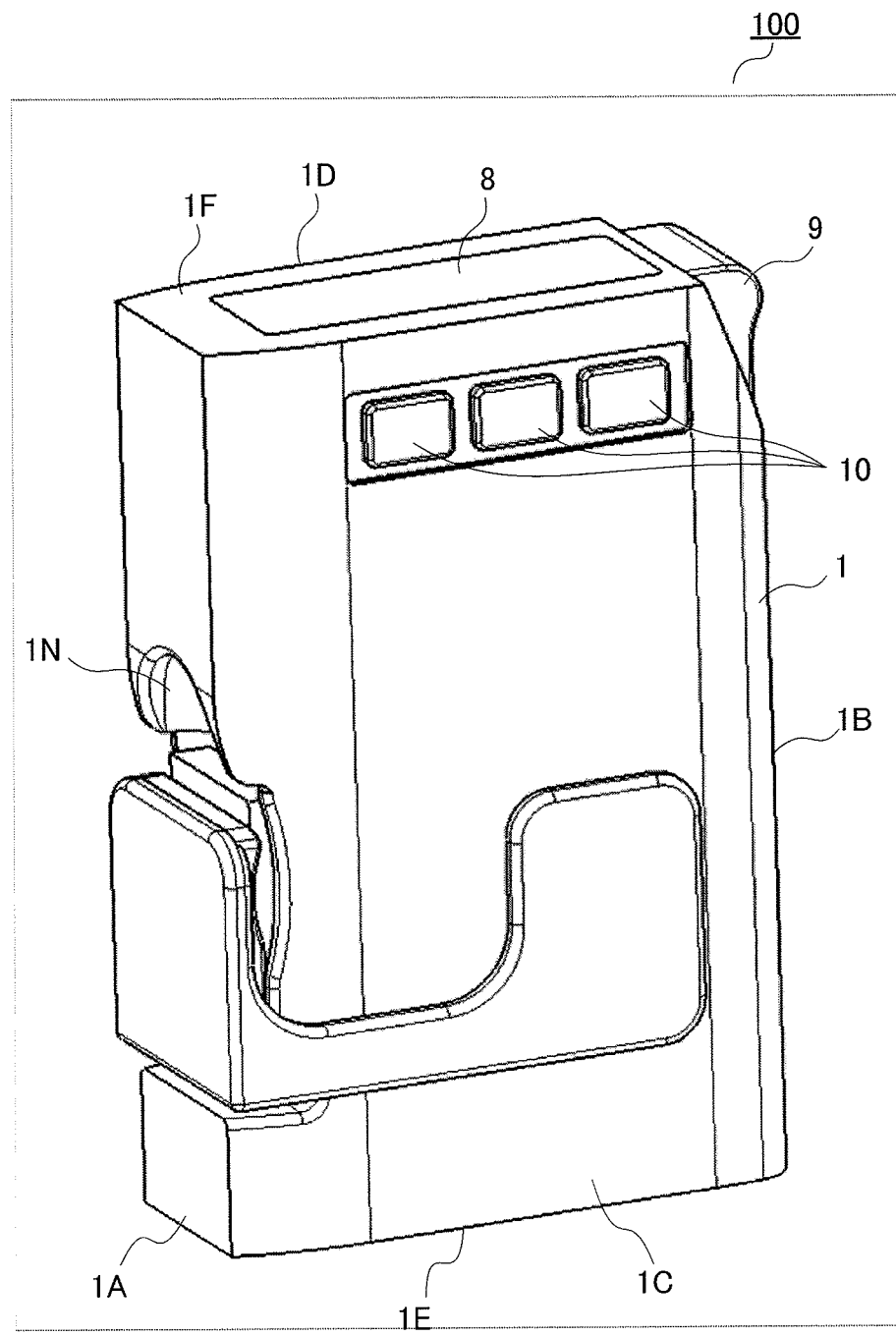
FIG. 1 is a perspective view showing a measurement device according to Embodiment 1 of the present invention.
Figure 2:
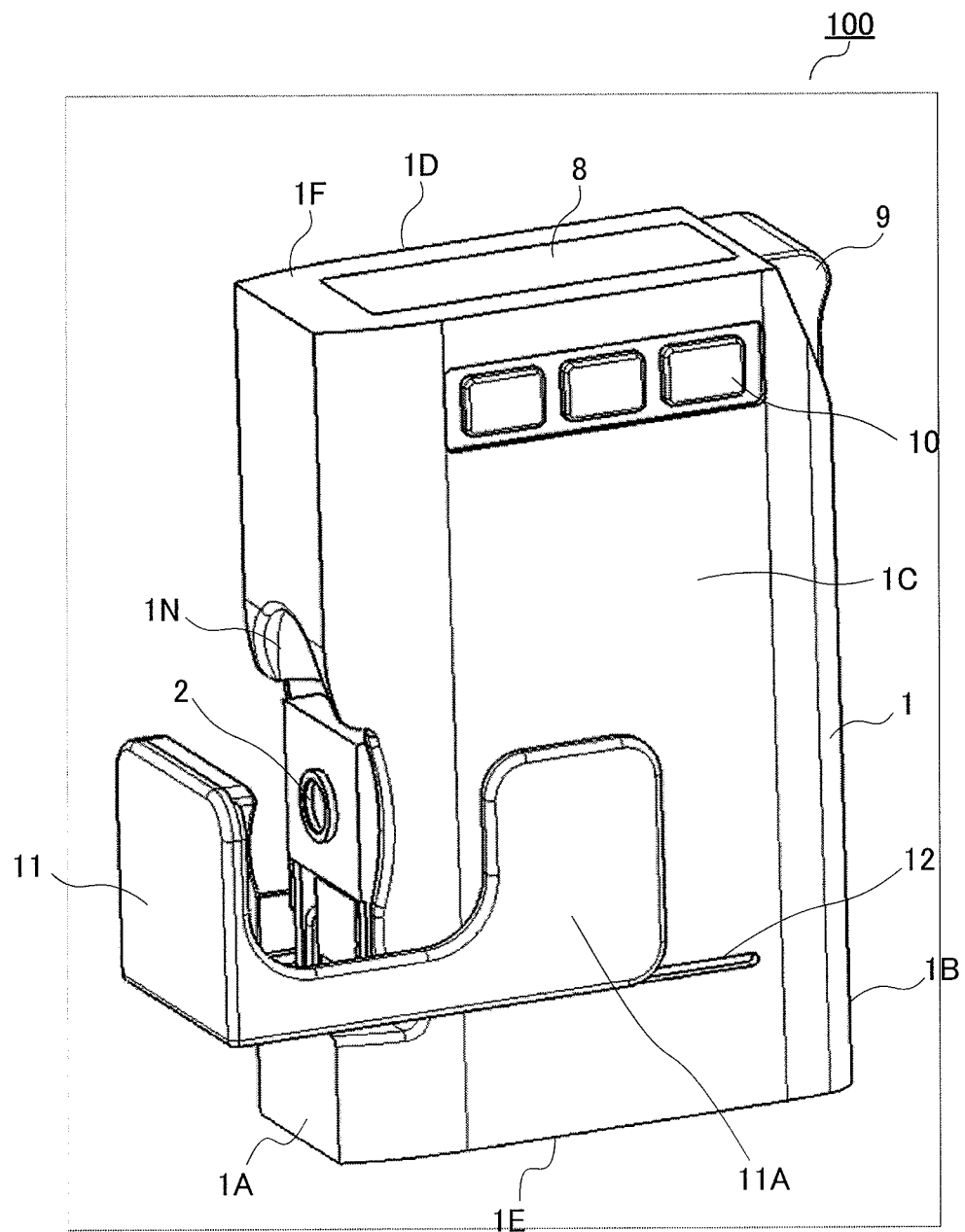
FIG. 2 is a perspective view showing the measurement device according to Embodiment 1.
Figure 3:
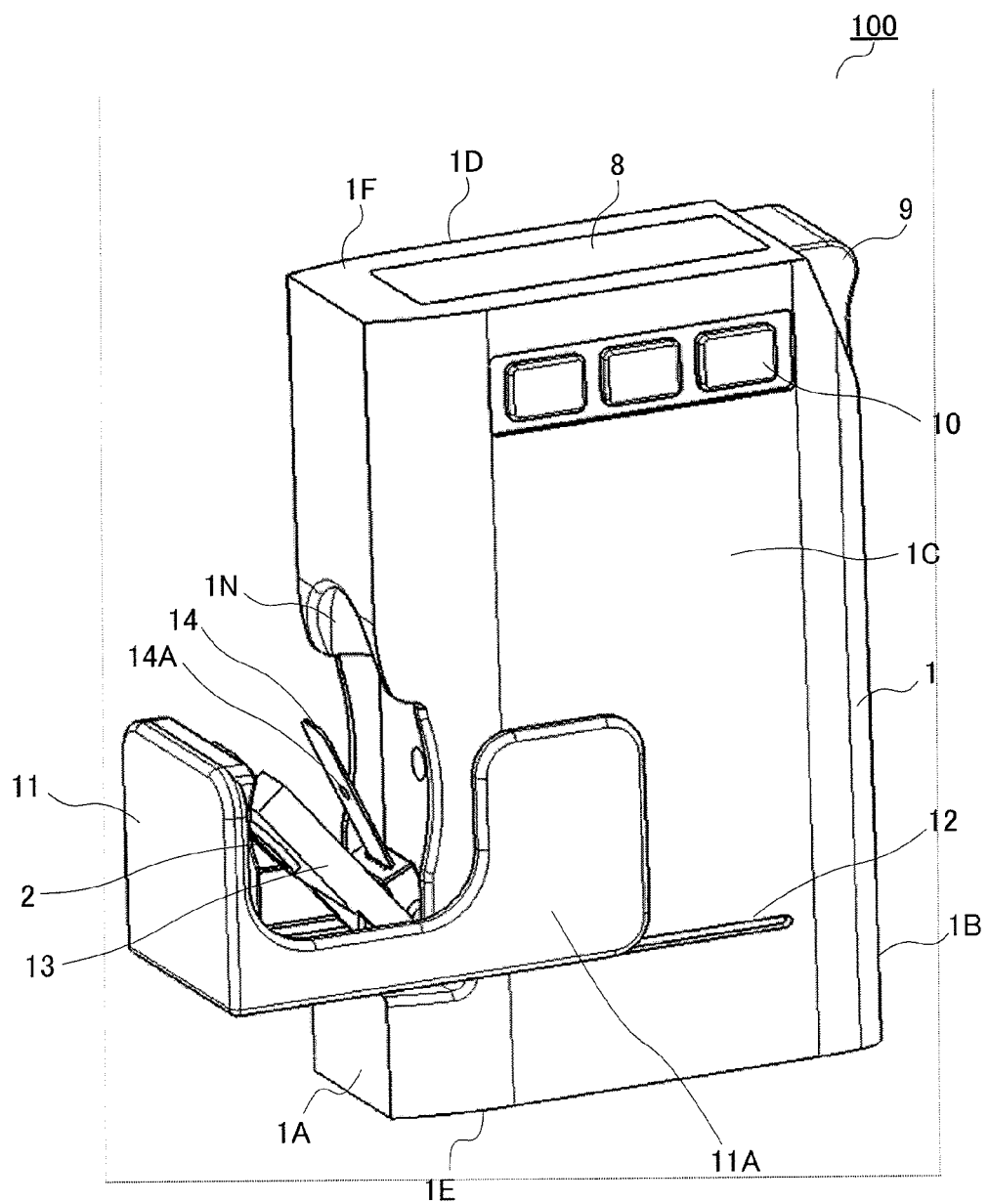
FIG. 3 is a perspective view showing the measurement device according to Embodiment 1.
Figure 4:
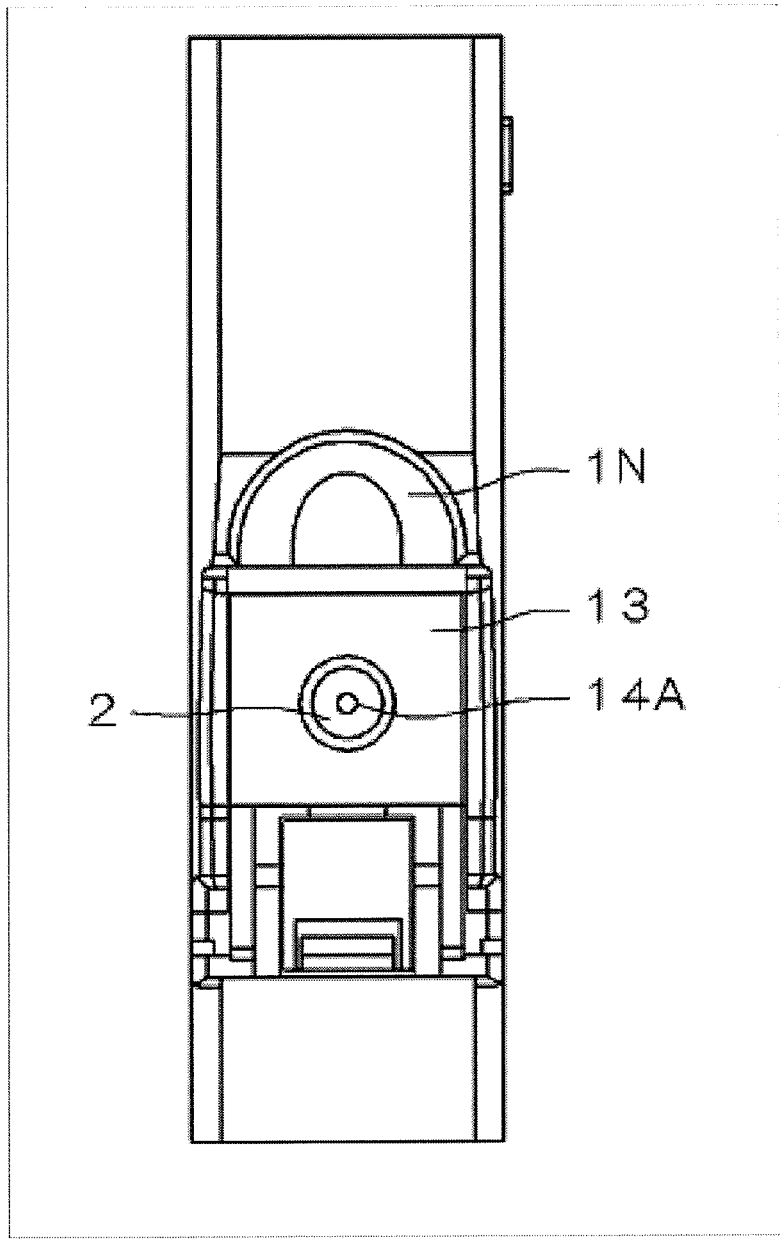
FIG. 4 is a front view of the measurement device according to Embodiment 1 as viewed from a front.
Figure 5:
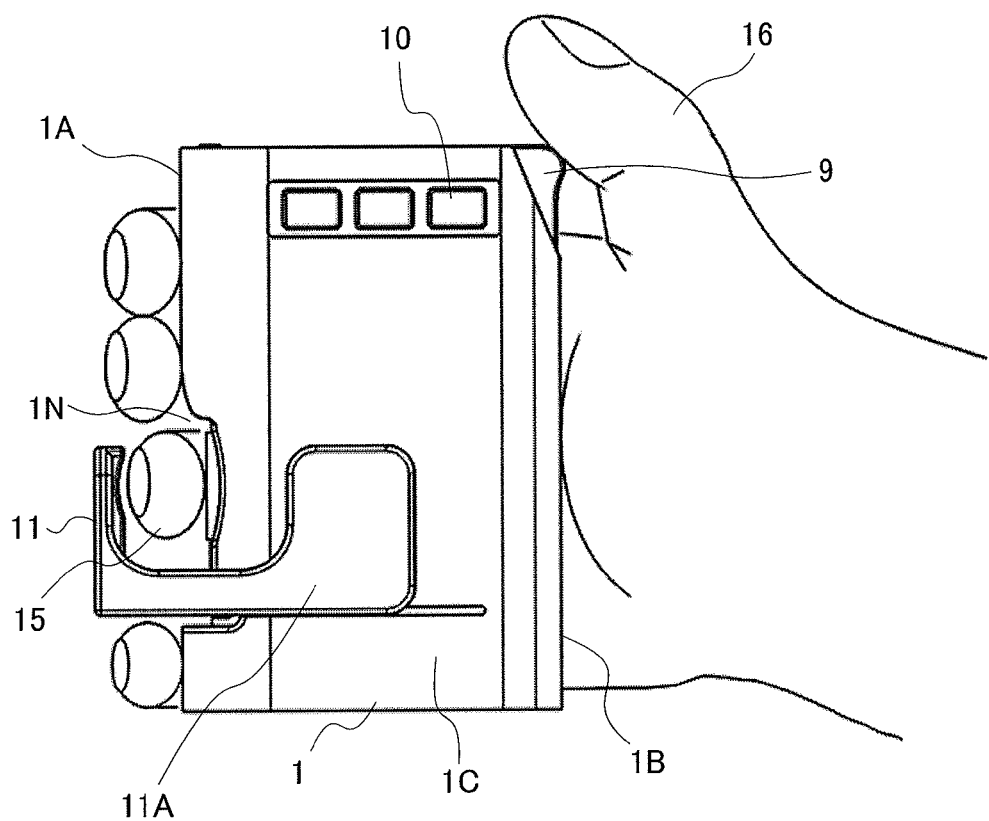
FIG. 5 is a perspective view illustrating a usage state of the measurement device according to Embodiment 1.
Figure 6:
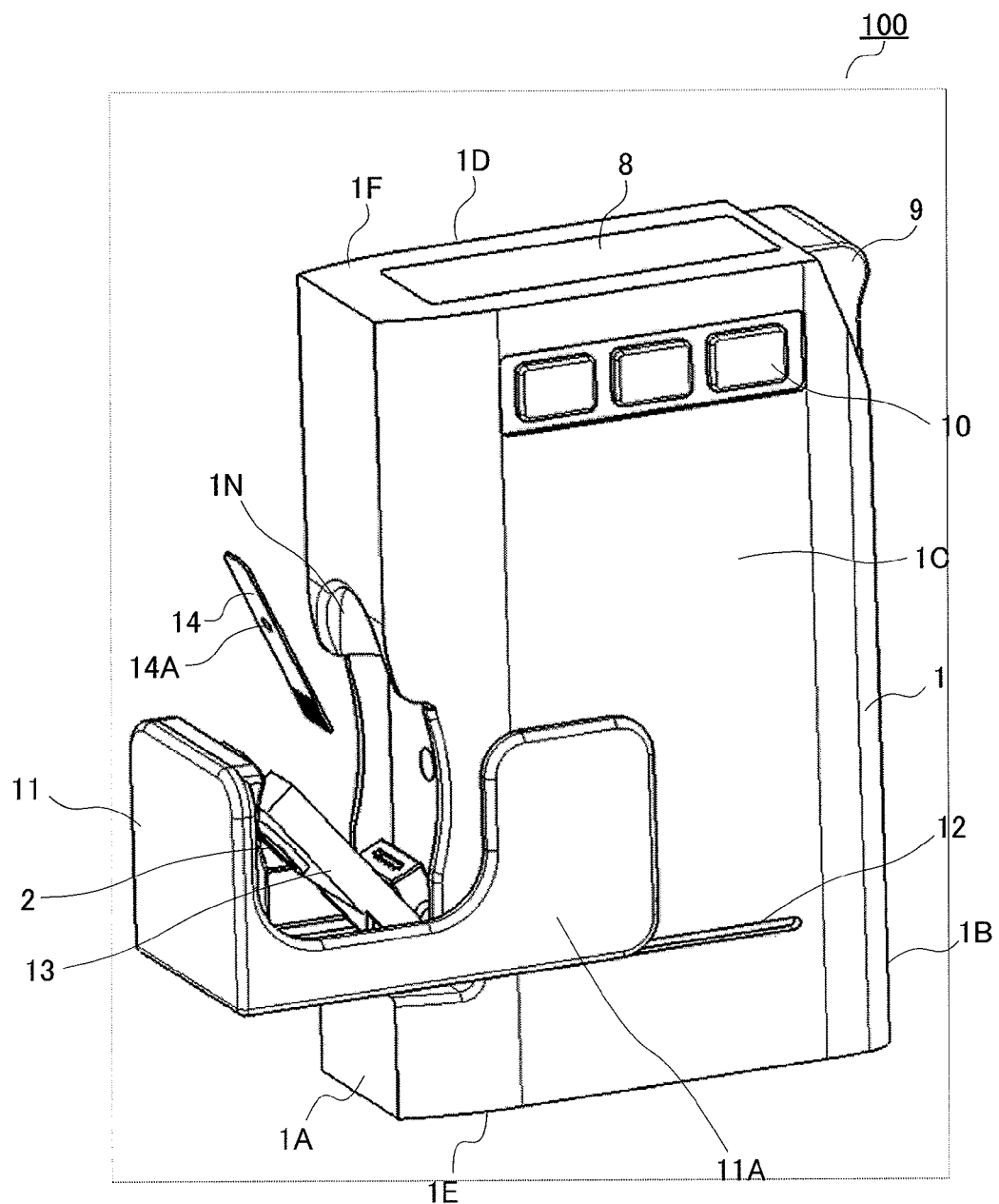
FIG. 6 is a perspective view illustrating the usage state of the measurement device according to Embodiment 1.

FIGS. 1 to 3 are perspective views showing a measurement device according to Embodiment 1 of the present invention. FIG. 4 is a front view of the measurement device as viewed from the front and FIGS. 5 and 6 are perspective views illustrating a usage state of the measurement device.

The present embodiment is an example in which the laser unit is applied to a blood glucose level measurement device to measure the blood glucose level.

As shown in FIGS. 1 to 4, measurement device 100 includes main body case 1 made of a rectangular tubular frame having upper and lower surfaces. The frame constituting main body case 1 has, as shown in FIGS. 1 and 2, front face 1A on the left side, rear face 1B on the right side, and side faces 1C and 1D on the front and rear sides respectively. In this state, the frame has a flat shape with the interval between front face 1A and rear face 1B wider than the interval between side faces 1C and 1D.

As shown in FIGS. 2 to 4, laser radiation hole 2 is formed on front face 1A side of main body case 1. Laser radiation hole 2 is provided in a horizontally central portion of front face 1A and lower than a vertically central portion of front face 1A. Laser unit 200 (see FIGS. 8 to 14, hereinafter the same) is arranged inside main body case 1 on the backward side of laser radiation hole 2.

As shown in FIGS. 1 to 3, liquid crystal type display section 8 is arranged on upper surface 1F of main body case 1. Starting switch 9 of laser unit 200 is arranged on the upper side of rear face 1B. Operation switch 10 is provided above side face 1C.

Operation switch 10 adjusts output of the laser. Operation switch 10 also performs an operation to check a history of the detected blood glucose level through display section 8.

As shown in FIGS. 2 and 3, cover 11 is arranged forward of laser radiation hole 2. Cover 11 has integrated support section 11A in a lower part on both sides. Support section 11A is slidably supported by slide groove 12 formed in both side faces 1C and 1D constituting main body case 1.

Cover 11 has a function as a protection cover against laser light shone from laser radiation hole 2. When no measurement is made, cover 11 is, as shown in FIG. 1, in a closed state by being brought closer to front face 1A of main body case 1. When measurement is made, cover 11 is, as shown in FIG. 2, in an open state by being further pulled forward of front face 1A. In both cases of non-measurement/measurement, cover 11 is present forward of laser radiation hole 2 to serve as a protection cover.

As shown in FIGS. 3 and 4, laser radiation hole 2 is formed above finger rest section 13. A lower part of finger rest section 13 is rotatably pivoted on main body case 1. When, as shown in FIG. 3, an upper part of finger rest section 13 is rotated forward, measuring sensor 14 to measure the blood glucose level is exposed. Measuring sensor 14 is removably mounted while the upper part of finger rest section 13 is rotated forward. In the present embodiment, measuring sensor 14 measures the blood glucose level.

As shown in FIG. 3, measuring sensor 14 has through hole 14A formed in a portion opposing laser radiation hole 2. Laser light emitted from the tip (left end in FIG. 9 described later) of laser rod 220 via condensing lens 207 (see FIG. 9) is shone into a fingertip of finger 15 shown in FIG. 5 via through hole 14A and laser radiation hole 2.

FIG. 5 shows a state of measuring the blood glucose level in a right hand. As shown in FIGS. 1 to 3, the upper part of finger rest section 13 is raised toward the backward side and in this state, main body case 1 is held, as shown in FIG. 5, in the right hand and finger 15 is pressed against finger rest section 13 to measure the blood glucose level.

Main body case 1 has a holding section to be held by the palm of a hand and a fingertip formed with front face 1A, rear face 1B, and side faces 1C and 1D. As shown in FIG. 5, one finger 15 is pressed to the front of laser radiation hole 2 to operate starting switch 9. Accordingly, laser light is shone into the finger 15 and blood outflows from a radiated portion.

The blood outflows to the side of through hole 14A of measuring sensor 14 due to a suction force from inside main body case 1. Measuring sensor 14 is a blood collecting means having a reagent near through hole 14A. Measuring sensor 14 sends a detection signal indicating a conduction state of the reagent to measurement device 100. Measurement device 100 measures the blood glucose level based on the detection signal and displays the measured blood glucose level in display section 8.

The present embodiment adopts a configuration in which blood caused to outflow by laser light radiation is supplied to the side of through hole 14A by a suction force, but for example, a configuration may be adopted in which blood is supplied to the side of through hole 14A by pressing finger 15 against the laser radiation hole 2 side by a pressurizing means (not shown) provided on the side of laser radiation hole 2 of cover 11 or pressing finger 15 against laser radiation hole 2 side by a force of finger 15 itself.

As shown in FIG. 6, measuring sensor 14 is removed from measurement device 100 for replacement after measuring the blood glucose level. The upper part of finger rest section 13 is tilted to the forward side and exposed measuring sensor 14 is pulled out by holding an upper part thereof between fingers. At this point, the lower part of cover 11 is integrated with support section 11A and thus, it is easy to pick up measuring sensor 14 or mount measuring sensor 14 shown in FIG. 3 via a space open above cover 11 (space formed by absence of support section 11A).

To increase the space (space formed by absence of support section 11A), recess 1N is formed in a portion of front face 1A of main body case 1 above laser radiation hole 2.

Figure 7:
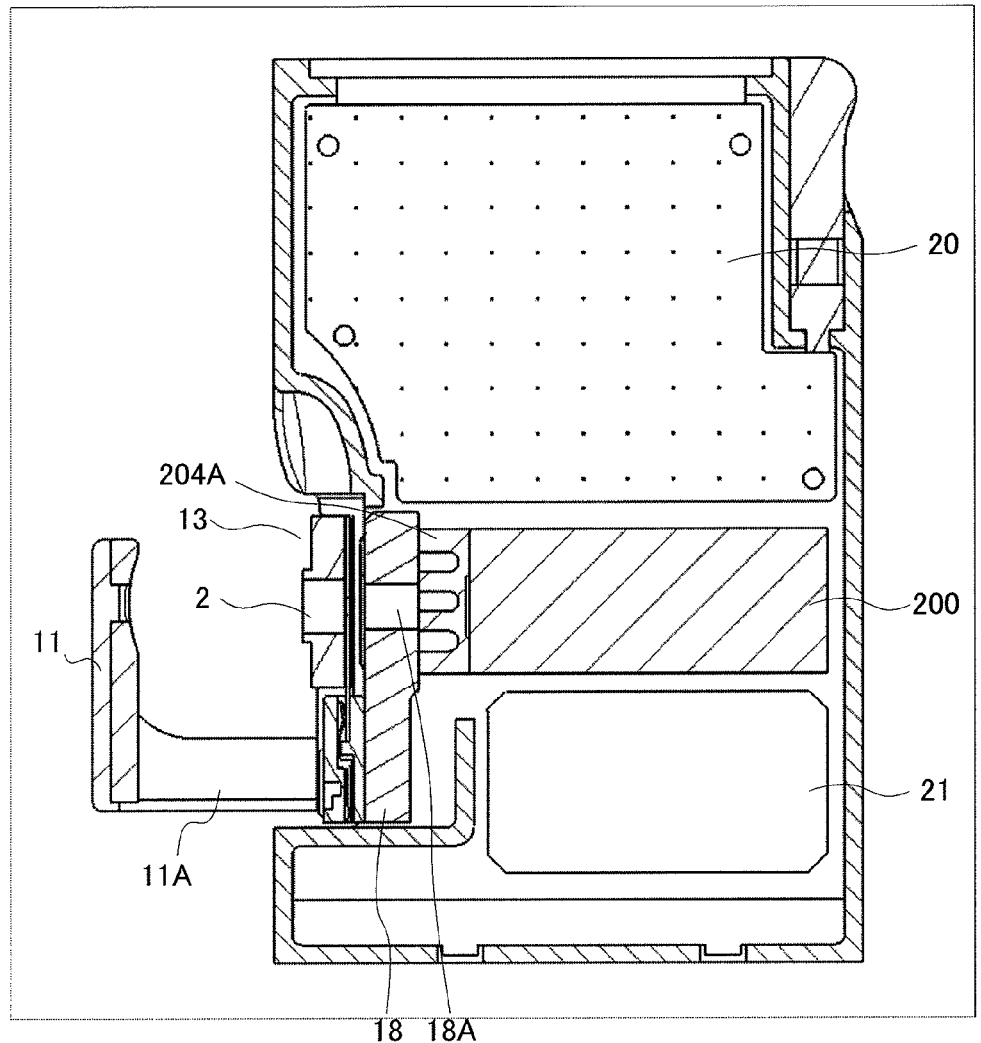
FIG. 7 is a side sectional view illustrating the usage state of the measurement device according to Embodiment 1.

FIG. 7 is a side sectional view illustrating the usage state of measurement device 100.

As shown in FIG. 7, laser unit 200 is arranged inside main body case 1 on the backward side of laser radiation hole 2. Moreover, electric circuit 20 is arranged above laser unit 200 and battery 21 is arranged below laser unit 200. Electric circuit 20 includes a high voltage generating circuit (not shown) that generates a high voltage to light a flash lamp.

Laser unit 200 is mounted in an upper part of mounting unit 18 by mounting section 204A integrated with a front portion of condensing lens 207 (see FIG. 9) by, for example, screwing. Countermeasures against vibration are taken by way of an elastic member (not shown) for the mounting. Finger rest section 13 is rotatably mounted on a lower part of mounting unit 18. Finger rest section 13 can be, as shown in FIGS. 2 and 6, freely opened and closed. Opening 18A is formed in a portion of mounting unit 18 opposing laser radiation hole 2 so that passage of laser light is not interfered with.

Figure 9:
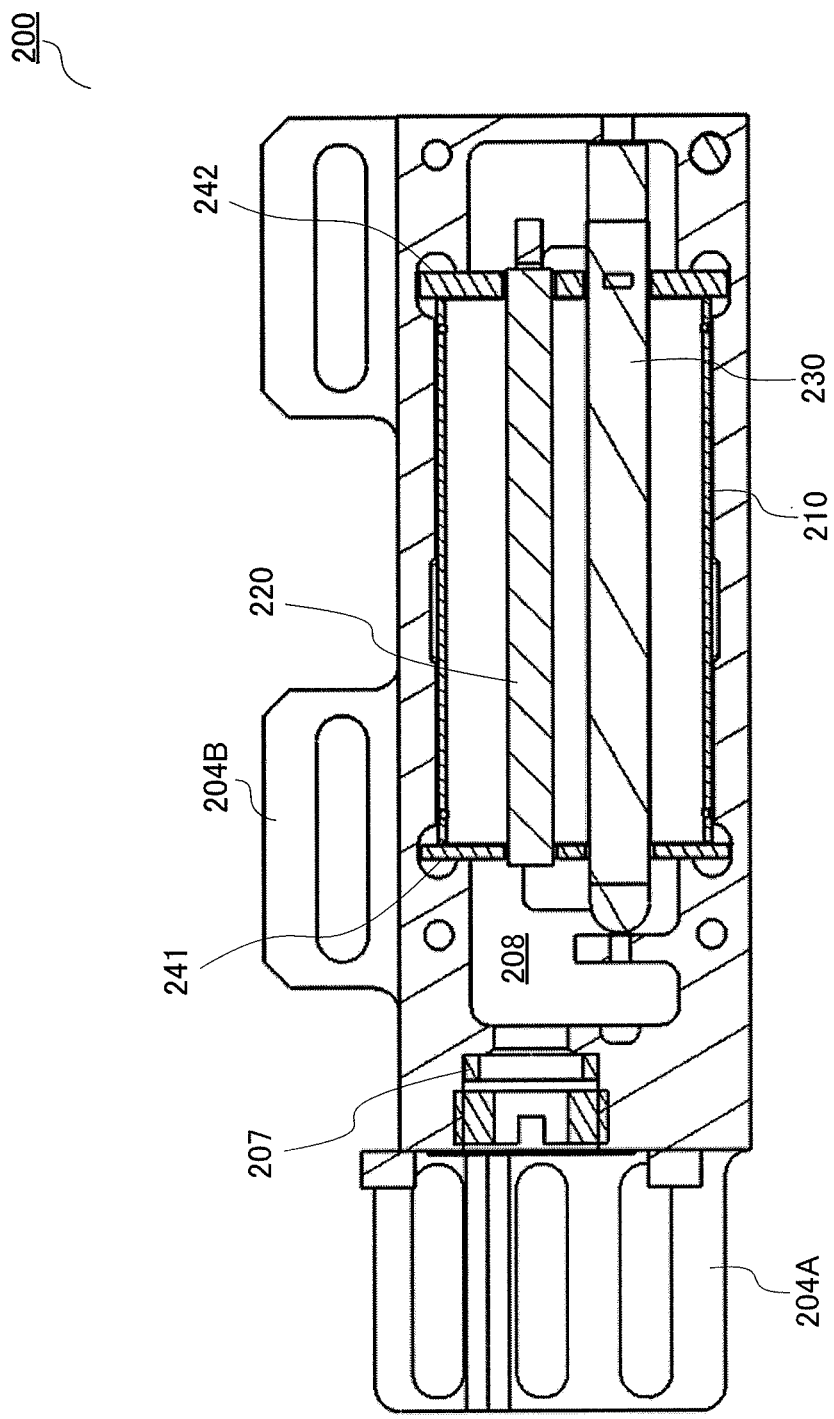
FIG. 9 is a sectional view taken along the line A-A of FIG. 8.

As shown in FIG. 9 described later, condensing lens 207 is integrated with laser unit 200 (lower case 202 constituting laser unit 200 shown in FIG. 10). Accordingly, the positional relationship with laser rod 220 provided inside laser unit 200 (lower case 202 constituting laser unit 200 shown in FIG. 10) is stabilized.

In the above description, measurement device 100 that measures blood components after puncturing a skin by mounting laser unit 200 and mounting blood sensor 14 has been described, but the present embodiment is not limited to this. For example, when blood sensor 14 is not mounted, measurement device 100 can be used as a laser puncturing device in which laser unit 200 to puncture a skin by laser is mounted. That is, the present embodiment can be applied to any apparatus that uses laser unit 200.

The present embodiment is characterized by the configuration of laser unit 200.

Laser unit 200 will be described in detail below.

Figure 8:
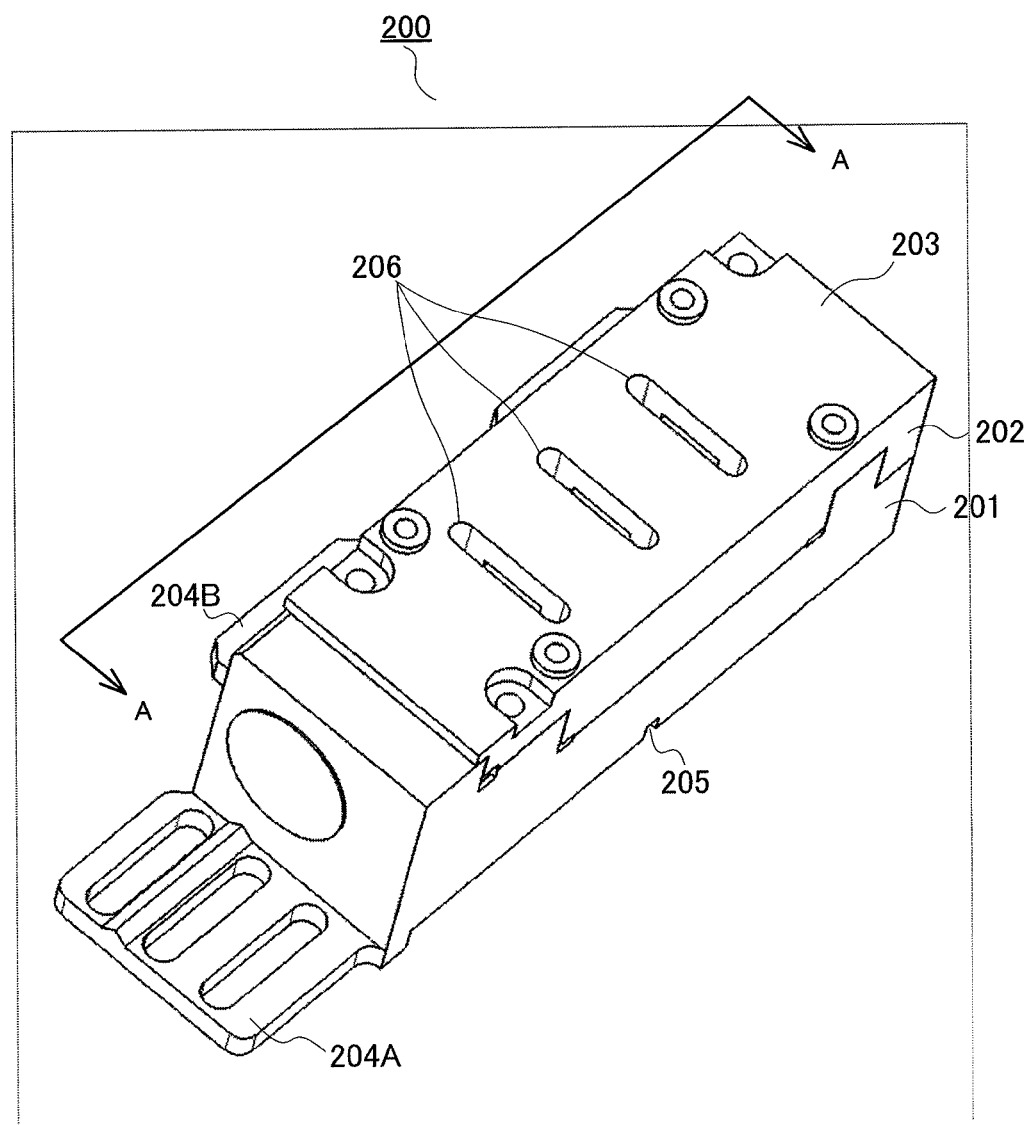
FIG. 8 is a perspective view showing a configuration of a laser unit of the measurement device according to Embodiment 1.

FIG. 8 is a perspective view showing the configuration of laser unit 200 and FIG. 9 is a sectional view taken along the line A-A of FIG. 8. FIGS. 10 to 14 are exploded perspective views of laser unit 200.

Figure 10:
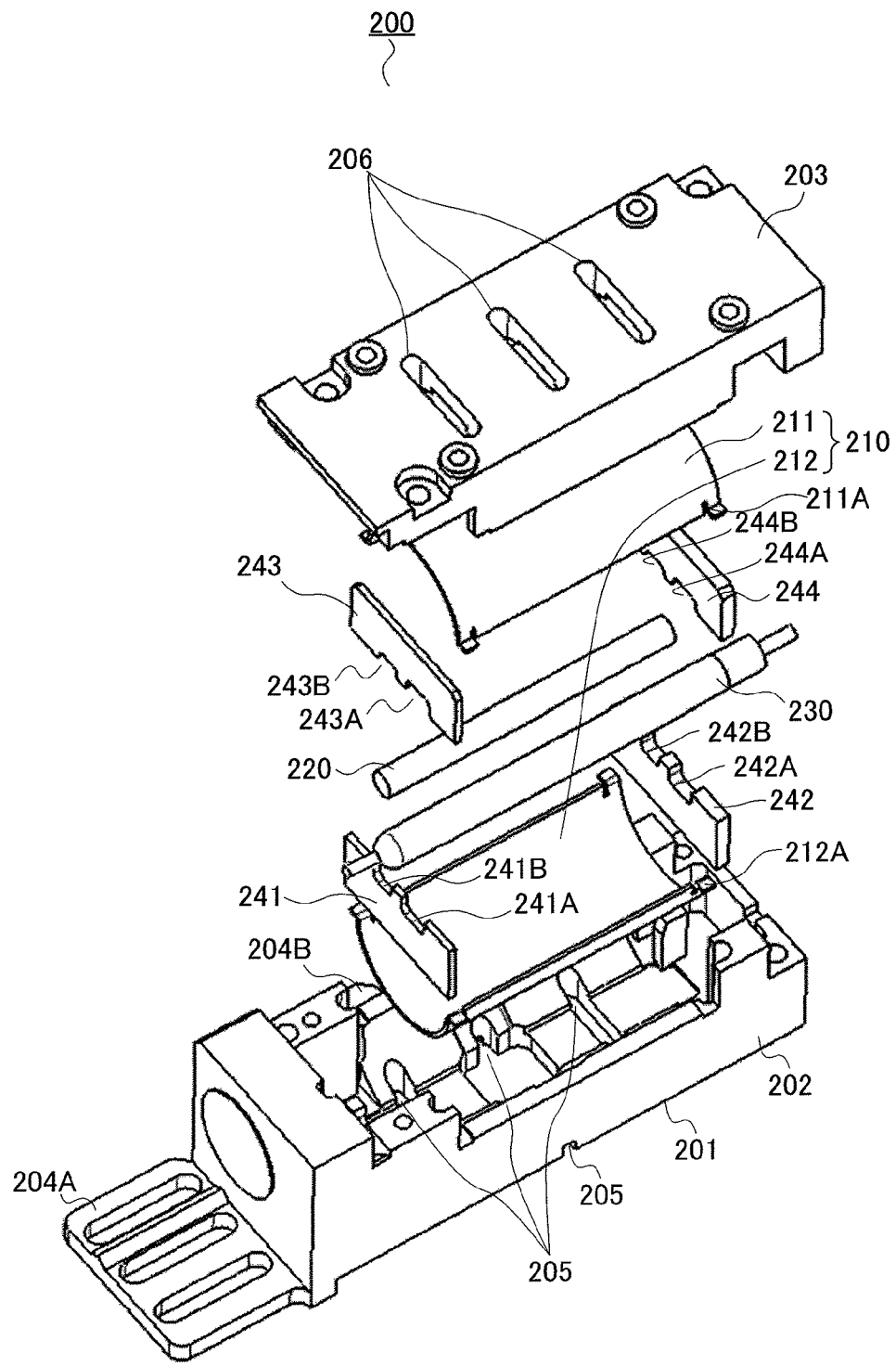
FIG. 10 is an exploded perspective view of the laser unit of the measurement device according to Embodiment 1.

As shown in FIGS. 9 and 10, laser unit 200 includes unit main body 201, lens-barrel 210 arranged inside unit main body 201, and laser rod 220 and flash lamp 230 arranged to oppose each other inside lens-barrel 210.

[Unit Main Body 201]

Unit main body 201 includes, as shown in FIG. 8, lower case 202 forming a lower part of the housing and upper case 203 mounted on lower case 202 and forming an upper part of the housing.

Lower case 202 has formed therein mounting sections 204A, 204B to mount unit main body 201 on mounting unit 18 inside main body case 1. Mounting section 204A extends forward from the bottom of lower case 202 and mounting section 204B extends to the side face from the bottom of lower case 202.

Vent hole 205 in a slit shape to dissipate heat inside unit main body 201 is provided in the lower surface of lower case 202 and vent hole 206 in a slit shape to dissipate heat inside unit main body 201 is provided in the upper surface of upper case 202.

Vent holes 205, 206 are provided to make heat dissipation by support media 241, 242, 243 and 244 described later more efficient.

[Lens-Barrel 210]

Lens-barrel 210 has, as shown in FIGS. 10 to 14, an elliptic shape and reflects light emitted from flash lamp 230 to condense the light to laser rod 220. Lens-barrel 210 is produced by machining a high-luminance aluminum sheet.

Lens-barrel 210 is formed by arranging, as shown in FIGS. 9 and 10, an elliptic cylinder whose vertical direction (direction of upper surface 1F and lower surface 1E of main body case 1 in FIG. 1) is longer than whose lateral direction (direction of side faces 1C and 1D of main body case) in a horizontal direction (front face 1A and rear face 1B of main body case 1 in FIG. 1).

Lens-barrel 210 has flash lamp 230 arranged below in the horizontal direction in the elliptic cylinder and laser rod 220 arranged above in the horizontal direction and opposite thereto. By arranging flash lamp 230 below laser rod 220, flash lamp 230 is brought closer to lower surface 1E of main body case 1, making it easier to take countermeasures against heat.

Lens-barrel 210 includes upper lens-barrel 211 in a dome shape and lower lens-barrel 212 in a dome shape, which are portions divided into upper and lower portions. Upper lens-barrel 211 and lower lens-barrel 212 have leg sections 211A, 212A respectively. Upper lens-barrel 211 and lower lens-barrel 212 cause leg sections 211A, 212A oppose each other to abut for integration of upper and lower portions. As a result, elliptic lens-barrel 210 is formed.

Upper lens-barrel 211 and upper lens-barrel 212 are made of a high-luminance aluminum material and at least an inner circumferential surface thereof is planished so that the inner side of upper lens-barrel 211 and lower lens-barrel 212 is in a state of extremely high reflectivity. Therefore, light emitted from flash lamp 230 is effectively supplied to laser rod 220.

[Laser Rod 220]

Laser rod 220 includes a reflector (not shown) on both end faces of the rod and receives light emitted from flash lamp 230 by an outer circumferential surface of laser rod 220 to amplify the light in energy inside laser rod 220. After predetermined energy is accumulated, laser rod 220 radiates laser light from the tip of laser rod 220. The tip side (left end side in FIGS. 9 and 10) of laser rod 220 is opposing laser radiation hole 2 via condensing lens 207.

The reflectivity of reflective coats on the end face of laser rod 220 is, for example, as follows.

Rear side: 99.5% or more

Emission side: 85% to 95%

[Flash Lamp 230]

Instead of a conventional quartz tube, hard glass tube 231 (see FIG. 15, hereinafter the same) is used as flash lamp 230. Flash lamp 230 emits light by sealing an inert gas in hard glass tube 231 in an elongated columnar shape and applying a high voltage to positive electrode 232 and negative electrode 233 (see FIG. 15, hereinafter the same) at both ends inside the hard glass tube.

(1) The fact that the hard glass tube has poor heat resistance compared to the quartz tube will be described.

While hard glass tube 231 has a linear expansion coefficient that causes an expansion of $30 \times 10^{-7}$ per meter when the temperature rises by 1° C., the quartz tube has a linear expansion coefficient that causes an expansion of $4 \times 10^{-7}$ per meter when the temperature rises by 1° C. When compared with the quartz tube, hard glass tube 231 has an extremely large linear expansion coefficient. Thus, unless heat of hard glass tube 231 is efficiently dissipated, the hard glass tube may be damaged by heat. In addition, when compared in terms of materials, the hard glass tube and the quartz tube have the following differences: While the softening temperature and hardness are increased by mixing boric acid with silicon, which is the main component of glass, and melting the mixture for the hard glass tube, the quartz tube is basically formed with silicon only. While the life in terms of the number of times of emission of a common small flash lamp is several tens of thousands times for the quartz tube, the life is 3,000 to 10,000 times for the hard glass tube. The hard glass tube is less resistant to heat than the quartz tube and is also inferior to the quartz tube in life in terms of the number of times of emission of a flash lamp.

(2) The arrangement of flash lamp 230 inside lens-barrel 210 also makes heat dissipation more difficult.

Flash lamp 230 preferably uses general-purpose members in terms of reducing the cost. For example, using a flashtube for a camera directly for flash lamp 230 can be considered. The flashtube of a camera has a reflector provided on the rear side, but the front side thereof is a heat dissipation surface and the temperature does not rise much so that thermal damage will not be caused. By contrast with this, the entire outer circumferential surface of flash lamp 230 is covered with lens-barrel 210 in laser unit 200. Thus, the temperature rise inside lens-barrel 210 is great and thermal damage may be caused if the mode in which the flash lamp used as a flashtube for a camera is directly used is adopted.

As described in (1) and (2), when the hard glass tube is used as a glass tube of flash lamp 230, it is necessary to take effective heat dissipation measures for the hard glass tube. In the present embodiment, the heat dissipation measures are taken by support media 241, 242, 243 and 244 supporting flash lamp 230 on unit main body 201.

Details of the structure of flash lamp 230 will be described later with reference to FIG. 15. Details of the relationship between the structure of flash lamp 230 and support media 241, 242, 243 and 244 (support members) will be described later with reference to FIG. 16.

[Support Media 241, 242, 243 and 244]

Flash lamp 230 is supported on unit main body 201 by plate support media 241, 242, 243 and 244 arranged outside lens-barrel 210.

Support media 241, 242, 243 and 244 (support members) support laser rod 220 and flash lamp 230 and position laser rod 220 and flash lamp 230 in radial direction inside lens-barrel 210.

Support media 241, 242, 243 and 244 are formed with members having high thermal conductivity such as metal and made of, for example, aluminum.

"Having high thermal conductivity" herein means being made of a material having a thermal conductivity of 100 W/(m·K) or higher. A "material of high thermal conductivity" means a material having a thermal conductivity of 100 W/(m·K) or higher. Support media 241, 242, 243 and 244 are characterized by being made of a material having a thermal conductivity of 100 W/(m·K) or higher.

Materials of support media 241, 242, 243 and 244 (support members) can be exemplified as follows:

Aluminum=236 W/(m·K)
Aluminum alloy=109 to 225 W/(m·K)
Copper=398 W/(m·K)
Brass=106 W/(m·K)

In the present embodiment, aluminum is used for support media 241, 242, 243 and 244 from the viewpoint of good workability and light weight.

Support media 241, 242, 243 and 244 have both a function to support flash lamp 230 on unit main body 201 and a function to dissipate heat from flash lamp 230 constituted by a hard glass tube having poor heat resistance. On the other hand, it is preferable to adopt a configuration that covers the light emitting surface of flash lamp 230 as little as possible. That is, a contact area between support media 241, 242, 243 and 244 and the outer circumferential surface of flash lamp 230 may be increased from the viewpoint of heat dissipation, but simply increasing the contact area reduces the light emitting surface of flash lamp 230.

Thus, in the present embodiment, a configuration is adopted in which support media 241, 242, 243 and 244 are brought into contact with the outer circumference of hard glass tube 231 (see FIG. 15) on positive electrode 232 and negative electrode 233 (see FIG. 15) at both ends of flash lamp 230. The position of the outer circumference of hard glass tube 231 on positive electrode 232 and negative electrode 233 at both ends of flash lamp 230 is where heat generation by positive electrode 232 and negative electrode 233 is the greatest and thus may have a large heat dissipation effect. The position of the outer circumference of hard glass tube 231 with which support media 241, 242, 243 and 244 are in contact is a portion of positive electrode 232 and negative electrode 233 and no light is emitted therefrom and therefore, a decrease in the light emitting surface can advantageously be minimized.

As described above, support media 241, 242, 243 and 244 are formed with a material having high thermal conductivity such as aluminum. Thus, heat on the outer circumferential surface of hard glass tube 231 (see FIG. 15) constituting flash lamp 230 can actively be discharged out of lens-barrel 210 via support media 241, 242, 243 and 244.

Support media 241, 242, 243 and 244 are in close contact with upper lens-barrel 211 and lower lens-barrel 212. Accordingly, heat transmitted to support media 241, 242, 243 and 244 can be dissipated to vent hole 205 via upper lens-barrel 211 and lower lens-barrel 212.

Surfaces of support media 241, 242, 243 and 244 facing an inner surface of lens-barrel 210 are planished to serve as reflecting surfaces. By using surfaces of support media 241, 242, 243 and 244 facing the inner surface of lens-barrel 210 as reflecting surfaces, the reflection effect of light inside lens-barrel 210 can be improved by causing reflection of lamp light inside lens-barrel 210.

Other features of laser unit 200 will be described with reference to FIGS. 8 and 9 again.

As shown in FIG. 9, lens-barrel 210 is tightly sealed to prevent intrusion of dust from outside the cabinet of laser unit 200. That is, upper lens-barrel 211 and lower lens-barrel 212 are brought into close contact to complete lens-barrel 210 and lens-barrel 210 is tightly sealed by being pressed down with the housing (housing including lower case 202 and upper case 203) after bringing support media 241, 242, 243 and 244 into contact with lens-barrel 210. A spring may be used in a pressing section of the housing. An enclosed space is secured by filling a gap between a feeding portion of a wire leading to flash lamp 230 and the housing with a silicon resin. With lens-barrel 210 tightly sealed in this manner, it is possible to prevent damage of the surface of the lens-barrel caused by burning of dust while adhering to the surface of lens-barrel 210 after light emission by the lamp.

If laser light is emitted while dust adheres to an end face of laser rod 220, the reflective coat deposited on the rod surface may be damaged. In the present embodiment, the space enclosed by the housing, support media 241 and 243 (support members), and condensing lens 207, which is defined as enclosed space 208, is tightly sealed to prevent intrusion of dust from outside the cabinet of laser unit 210. That is, as shown in FIG. 8, the tip surface (left side surface in FIG. 9) of laser rod 220 is exposed to the side of condensing lens 207 from support media 241 and 243 and thus, if dust adheres to the tip surface, sticking may occur. Thus, enclosed space 208 is created between support media 241 and 243 of lower case 202 and condensing lens 207 by covering an upper opening of lower case 202 with upper case 203. Then, vent hole 206 of upper case 203 and enclosed space 208 block a state of ventilation by using support medium 243. Damage of the reflective coat of laser rod 220 can be prevented by enclosed space 208.

On the rear side of laser rod 220, by contrast, no laser light is emitted and thus more adhesion of dust is allowed than on the front side and a slight gap is allowed. Thus, the thickness or the like of support members (here, support media 242 and 244) on the rear side may be increased.

Example

An example of outer dimensions of laser unit 200 will be illustrated.

Unit main body 201 has a rectangular parallelepiped shape with the width of 14 mm, the height of 14 mm, and the depth of 43 mm. Laser rod 220 has a columnar shape with the diameter of 1.5 mm to 3 mm and the length of 20 mm to 30 mm. Hard glass tube 231 (see FIG. 15) of flash lamp 230 has a columnar shape with the outside diameter of 2.5 mm to 3.5 mm and the length of 30 mm. The length (arc length) between positive electrode 232 and negative electrode 233 (see FIG. 15) of flash lamp 230 of a portion where flash lamp 230 emits light is 20 mm to 21 mm. The length of lens-barrel 210 is 20 mm to 21 mm. The thickness of support media 241, 242, 243 and 244 is 0.5 mm to 2 mm.

Next, how to assemble laser unit 200 will be described.

The process from the state shown in FIG. 10 to the completion of assembly in FIG. 8 through FIGS. 11 to 14 will be described.

Figure 11:
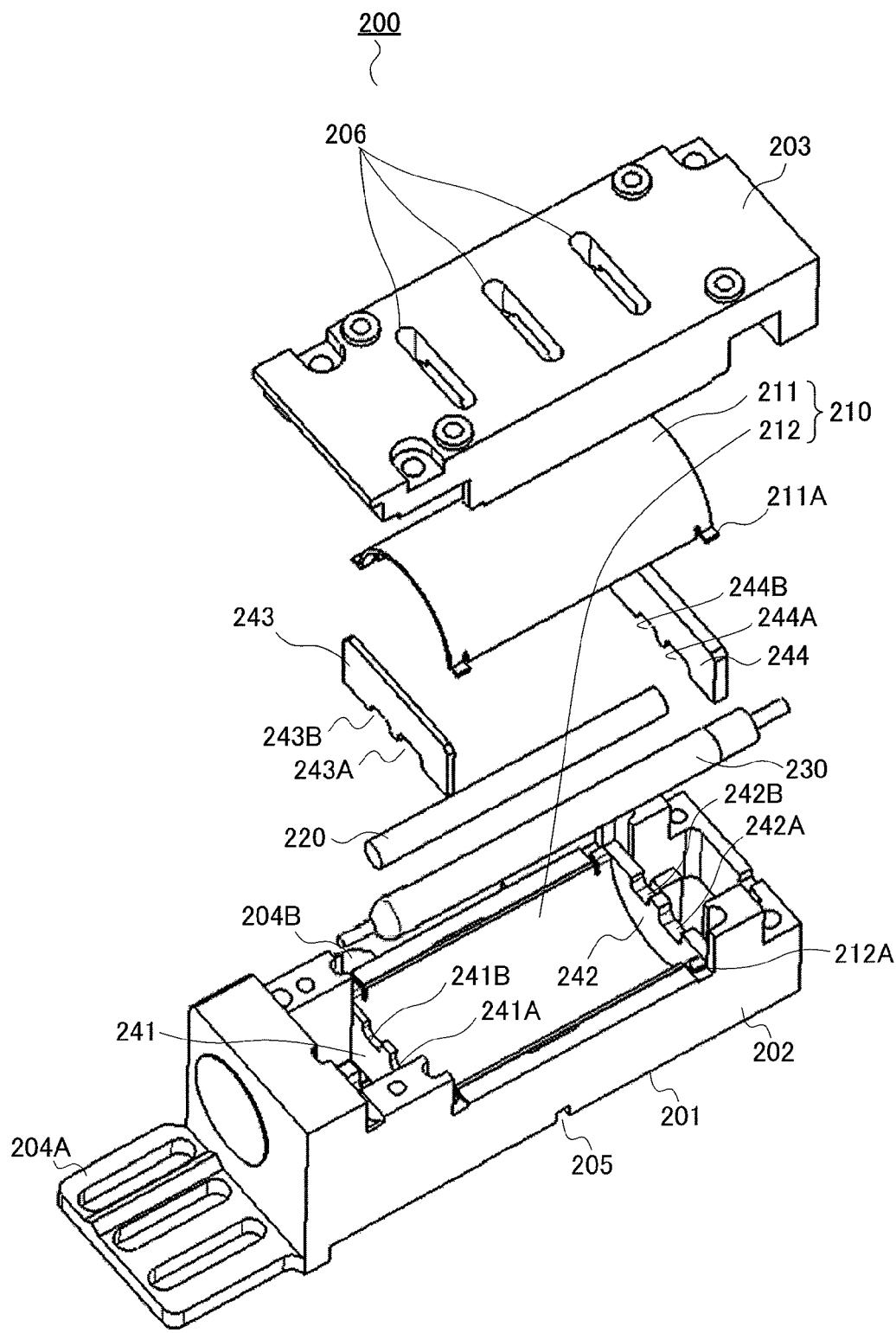
FIG. 11 is an exploded perspective view of the laser unit of the measurement device according to Embodiment 1.

As shown in FIG. 11, support media 241 and 242 are mounted on front and rear surfaces of lower lens-barrel 212 inside lower case 202, respectively. Lower lens-barrel 212 is pushed between support media 241 and 242 to house lower lens-barrel 212 in lower case 202.

Figure 12:
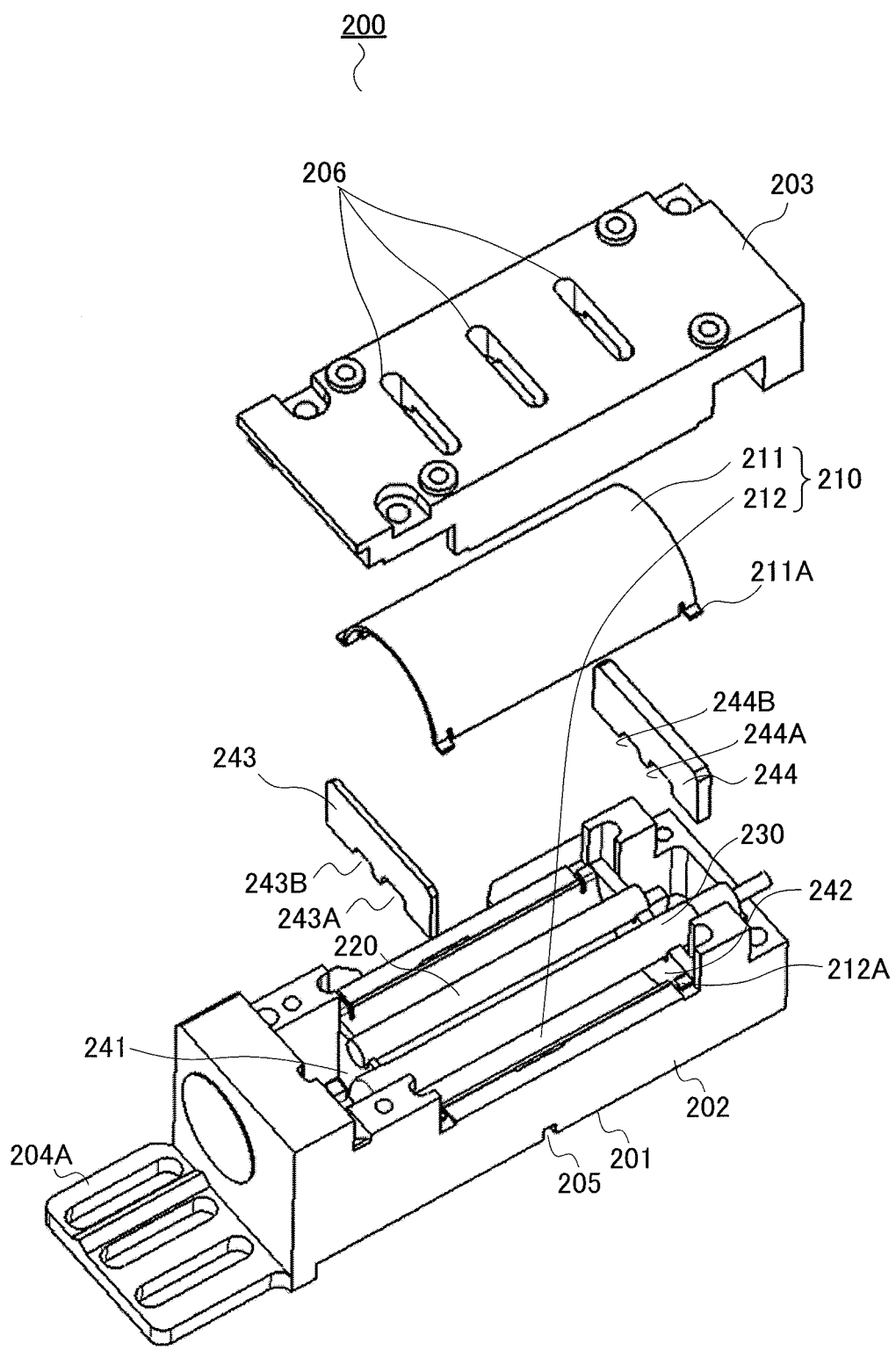
FIG. 12 is an exploded perspective view of the laser unit of the measurement device according to Embodiment 1.

As shown in FIG. 12, support media 241 and 242 have rectilinear recesses 241A and 241B, and 242A and 242B formed therein, respectively. Lower parts of outer circumferential surfaces of flash lamp 230 and laser rod 220 are placed on recesses 241A and 241B, and 242A and 242B of support media 241 and 242, respectively. Particularly, the outer circumferences of the hard glass tube corresponding to the positions of positive electrode 232 and negative electrode 233 (see FIG. 15) at both ends of flash lamp 230 are arranged in recess 241A of support medium 241 and recess 242A of support medium 242.

The reason for forming rectilinear recesses 241A and 241B, and 242A and 242B is as follows. Rectilinear notch sections are suitable for achieving accuracy of finishing when members of metal (aluminum) are finished. Also, assembly errors can be reduced due to the presence of flat surfaces. If the notch section is round, it is difficult to achieve accuracy of finishing like outer dimensions of laser rod 220 and flash lamp 230. If accuracy of finishing is not achieved, the accuracy of position of flash lamp 230 and laser rod 220 cannot be maintained, leading to lower laser output. Rectilinear notch sections are adopted from the viewpoint of ease of embodiment and cost reduction. However, round notch sections may of course be adopted.

Figure 13:
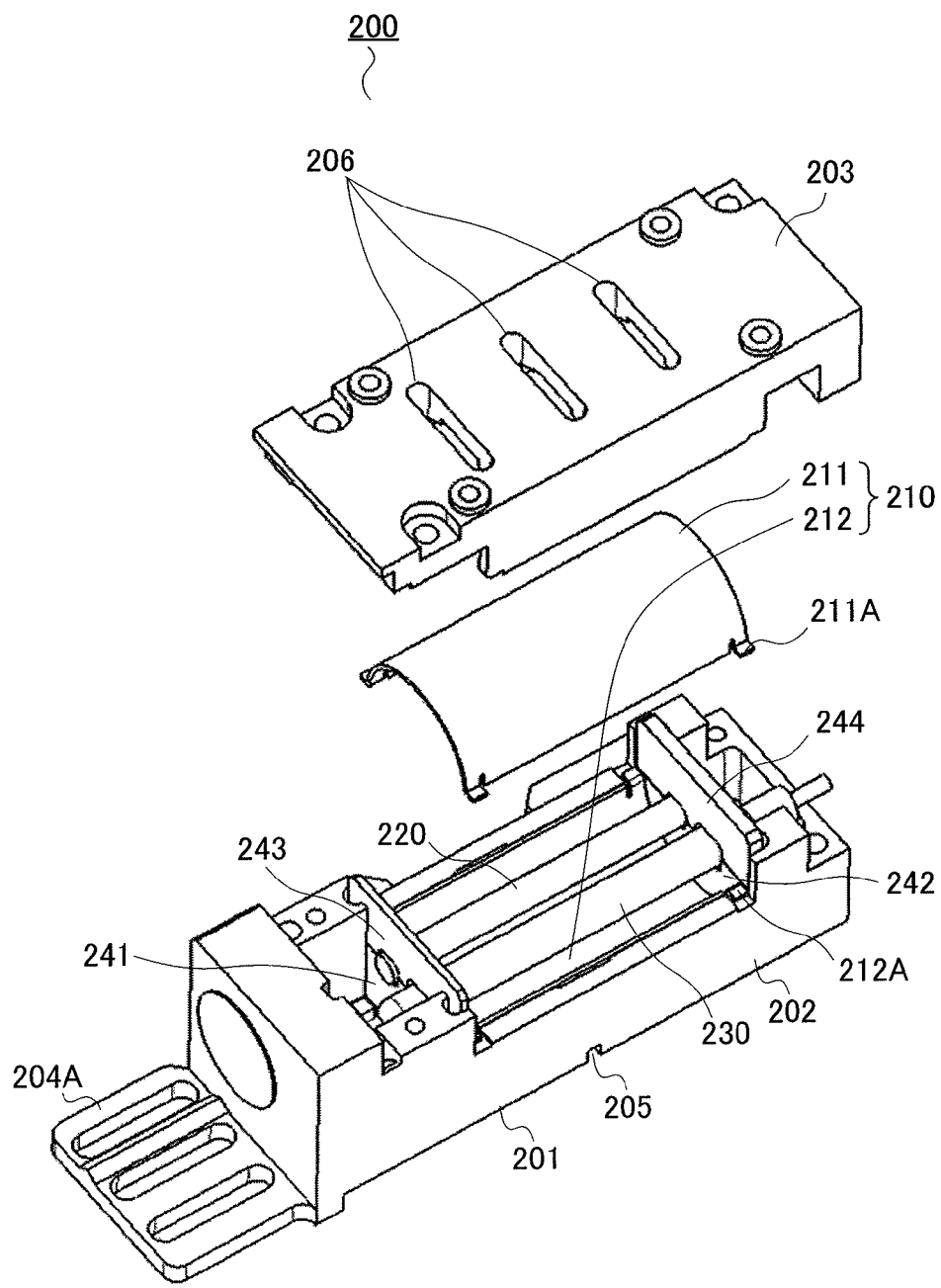
FIG. 13 is an exploded perspective view of the laser unit of the measurement device according to Embodiment 1.

As shown in FIG. 13, rectilinear recesses 243A and 243B, and 244A and 244B formed in support media 243 and 244 are mounted on, so as to cover, upper parts of outer circumferential surfaces of flash lamp 230 and laser rod 220 placed on recesses 241A and 241B, and 242A and 242B of support media 241 and 242, respectively.

Upper lens-barrel 211 is pushed between support media 243 and 244 to cause upper lens-barrel 211 to abut on lower lens-barrel 212 without any gap. With upper lens-barrel 211 and lower lens-barrel 212 abutted for integration of upper and lower portions, elliptic lens-barrel 210 is completed (state in FIG. 14).

Figure 14:
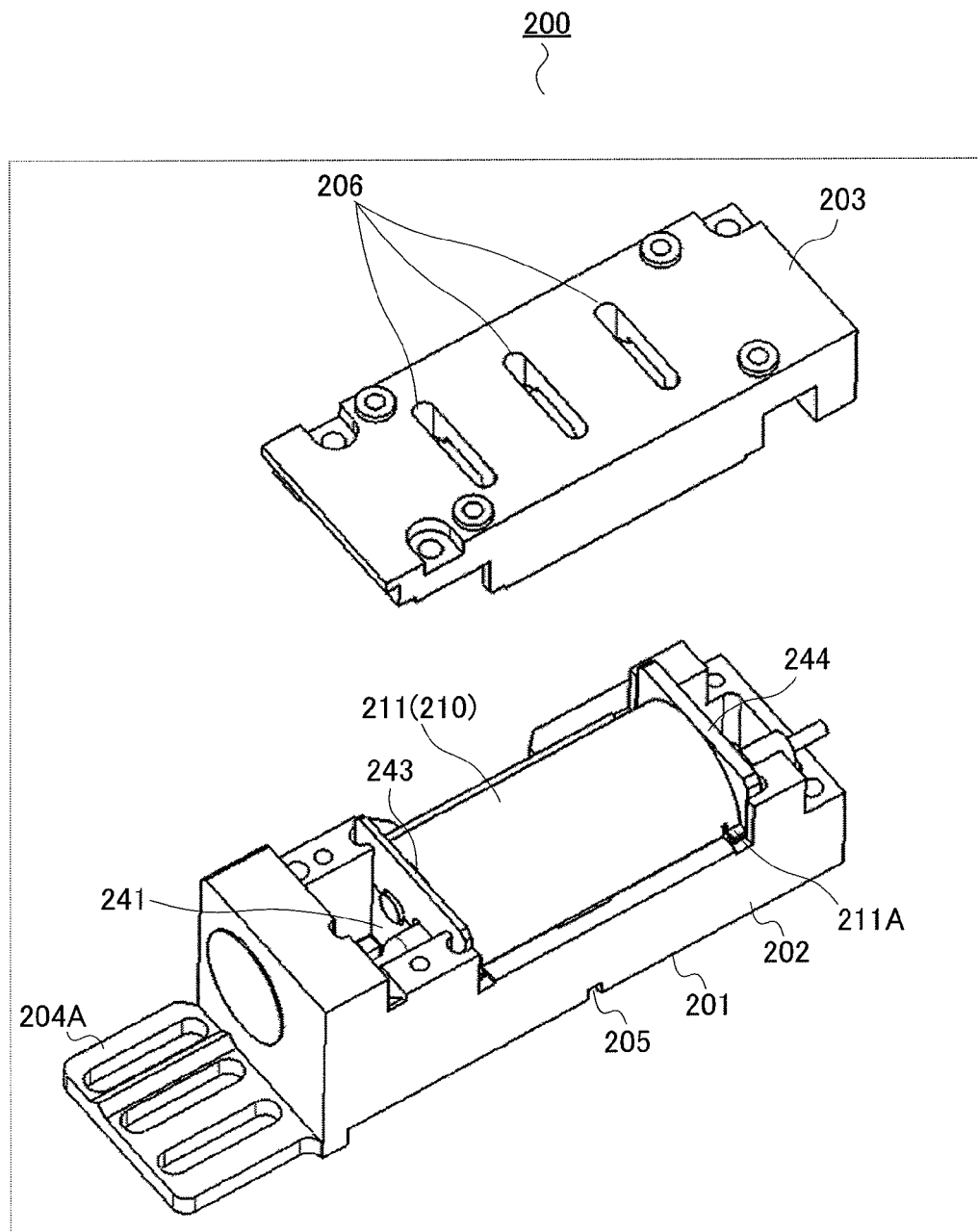
FIG. 14 is an exploded perspective view of the laser unit of the measurement device according to Embodiment 1.

As shown in FIG. 14, upper case 203 is mounted on the upper opening of lower case 202 to complete the assembly of laser unit 200 (state in FIG. 8).

Thus, laser unit 200 can be assembled by simply stacking each member in the order of FIGS. 10 to 14 and further FIG. 8. The configuration of laser unit 200 has advantages of allowing easy assembly and high productivity.

In the present embodiment, lens-barrel 210 is formed with upper lens-barrel 211 and lower lens-barrel 212. Support media 241, 242, 243 and 244 are arranged in front and rear openings of lens-barrel 210 in a pressed state. The front and rear openings of lens-barrel 210 are tightly sealed by support media 241 and 243 and support media 242 and 244 forming a pair vertically. Flash lamp 230 and laser rod 220 are arranged to oppose each other at predetermined intervals inside lens-barrel 210 tightly sealed by support media 241 and 243 and support media 242 and 244.

Lower case 202 has energizing sections (not shown) to energize support media 241, 242, 243 and 244 in openings at both ends of lens-barrel 210. Thus, air tightness is high and intrusion of dust into lens-barrel 210 can be prevented. A decrease in laser generation efficiency can be prevented by preventing sticking of dust to flash lamp 230.

The structure of flash lamp 230 will be described in more detail.

Figure 15:
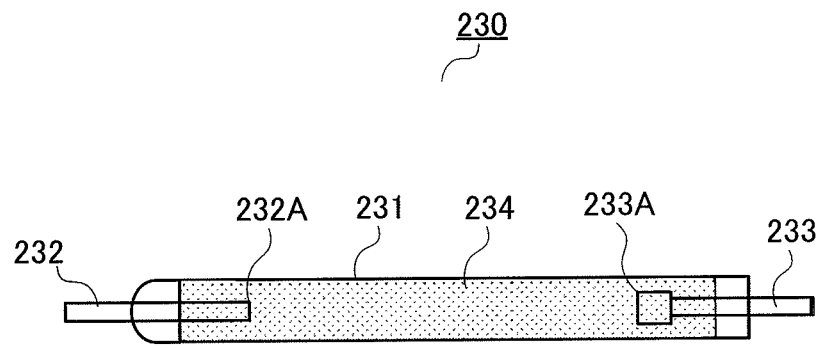
FIG. 15 schematically shows a structure of a flash lamp of the laser unit of the measurement device according to Embodiment 1.

FIG. 15 schematically shows the structure of flash lamp 230.

As shown in FIG. 15, flash lamp 230 includes hard glass tube 231 in a cylindrical tube shape, positive electrode 232 having positive electrode tip section 232A protruding into the tube, negative electrode 233 having negative electrode tip section 233A protruding into the tube, and transparent conductive coat 234 (see a shaded area) coating the surface around the outer wall of the hard glass tube between electrodes 232, 233, and an inert gas is sealed inside the tube.

Portions at both ends of hard glass tube 231 are filled with hard glass and a solid line inside the tube represents a boundary line between the hard glass and space.

Negative electrode 233 is connected to a 0 V potential and a high voltage of 250 V to 350 V is applied to positive electrode 232. Transparent conductive coat 234 made of tin oxide or titanium oxide is deposited on the surface around the outer wall of the hard glass tube between positive electrode 232 and negative electrode 233.

Tips of positive electrode 232 and negative electrode 233 are arranged to be present inside hard glass tube 231 and flash lamp 230 emits light between positive electrode tip section 232A of positive electrode 232 and negative electrode tip section 233A of negative electrode 233.

That is, with a high voltage (trigger voltage) of 3 to 4 kV applied to transparent conductive coat 234, flash lamp 230 emits light triggered by the high voltage Next, the relationship between the structure of flash lamp 230 and support media 241, 242, 243 and 244 will be described.

Figure 16:
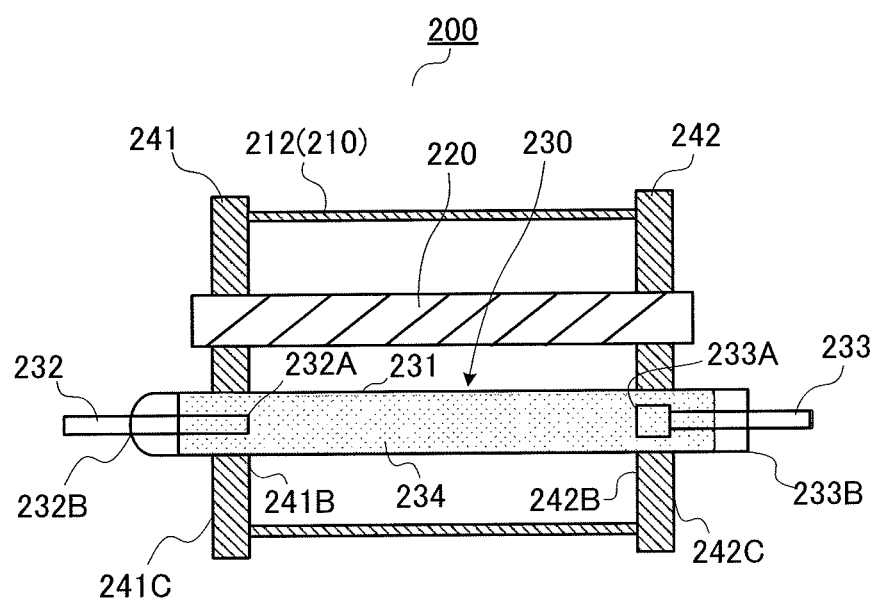
FIG. 16 is a sectional view of a principal section of the laser unit illustrating positional relationships between the flash lamp and a support medium of the laser unit of the measurement device according to Embodiment 1.

FIG. 16 is a sectional view of a principal section of laser unit 200 illustrating the positional relationships between flash lamp 230 and support media 241, 242, 243 and 244.

As shown in FIG. 16, laser rod 220 and flash lamp 230 are supported by support media 241 and 242 mounted on the front and rear sides outside lower lens-barrel 212. Though not illustrated, the relationship between upper lens-barrel 211 and support media 243 and 244 is the same. For ease of explanation, support media 243 and 244 not illustrated in FIG. 16 will also be described below together with support media 241 and 242.

Face 241B of support medium 241 facing the inner surface of lens-barrel 210 and face 242B of support medium 242 facing the inner surface of lens-barrel 210 oppose each other inside lens-barrel 210. Positive electrode 232 protrudes from surface 241C on the other side of face 241B of support medium 241 facing the inner surface of lens-barrel 210 and negative electrode 233 protrudes from surface 242C on the other side of face 242B of support medium 242 facing the inner surface of lens-barrel 210. Boundary section 232B between positive electrode 232 and hard glass tube 231 is formed and boundary section 233B between negative electrode 233 and hard glass tube 231 is formed.

Face 242B of support medium 242 facing the inner surface of lens-barrel 210 is positioned in tip section 233A of negative electrode 233 and face 241B of support medium 241 facing the inner surface of lens-barrel 210 is positioned in tip section 232A of positive electrode 232. In view of the above and the fact that flash lamp 230 emits light between tip section 232A of positive electrode 232 and tip section 233A of negative electrode 233, light emitted from flash lamp 230 is effectively supplied to laser rod 220 without being blocked by support media 241, 242, 243 and 244 (support members).

The positional relationships between flash lamp 230 and support media 241, 242, 243 and 244 will be described with reference to FIG. 16.

The front and back of lens-barrel 210 contact and electrically conduct with support media 241, 242, 243 and 244. Support media 241, 242, 243 and 244 support flash lamp 230 while staying in contact with hard glass tube 231. Transparent conductive coat 234 on the surface of hard glass tube 231 and support medium 242 are electrically conducting.

The trigger voltage serving as a trigger to cause light emission of flash lamp 230 is applied to lens-barrel 210 from a high-voltage generation circuit (not shown). The trigger voltage is applied to transparent conductive coat 234 through support media 241, 242, 243 and 244 conducting to lens-barrel 210.

If the distance between boundary section 232B between positive electrode 232 and hard glass tube 231, and support medium 241 and support medium 243 (not shown) is short (proportion of 1 mm or less for a potential difference of 1 kV), a discharge occurs between positive electrode 232 and support medium 241 and support medium 243 due to the potential difference between support medium 241 and support medium 243 (not shown) and positive electrode 232, which disrupts normal light emission of flash lamp 230. Similarly, if the distance between boundary section 233B between negative electrode 233 and hard glass tube 231, and support medium 242 and support medium 244 (not shown) is short (proportion of 1 mm or less for a potential difference of 1 kV), a discharge occurs between positive electrode 232 and support medium 242 and support medium 244 due to the potential difference between support medium 242 and support medium 244 and negative electrode 233, which disrupts normal light emission of flash lamp 230.

In view of the above circumstances, surface 242C on the other side of face 242B of support medium 242 facing the inner surface of lens-barrel 210 is positioned 3 to 4 mm away from boundary section 233B between negative electrode 233 and hard glass tube 231 to prevent unnecessary discharge. Also, surface 241C on the other side of face 241B of support medium 241 facing the inner surface of lens-barrel 210 is positioned 3 to 4 mm away from boundary section 232B between positive electrode 232 and hard glass tube 231 to prevent unnecessary discharge.

According to the present embodiment, as described above in detail, laser unit 200 of measurement device 100 includes lens-barrel 210 and laser rod 220 arranged inside lens-barrel 210. Further, laser unit 200 includes flash lamp 230 arranged to oppose laser rod 220 inside lens-barrel 210 and having an inert gas sealed inside hard glass tube 231, and support media 241, 242, 243 and 244, at least a portion of which is arranged outside lens-barrel 210 and which support the outer circumferential surface of hard glass tube 231 on the housing, are made of a material having a thermal conductivity of 100 W/(m·K) or higher.

Accordingly, heat of hard glass tube 231 can actively be dissipated out of lens-barrel 210 via support media 241, 242, 243 and 244 so that hard glass tube 231 can be prevented from being damaged by heat. The present inventors have conducted endurance tests against heat by repeatedly causing flash lamp 230 to emit light to confirm the effect thereof.

Because hard glass tube 231 that is far cheaper than a quartz glass tube can be used for flash lamp 230 of laser unit 200, a significant cost reduction of the measurement device and puncturing device using such a laser unit can be realized.

Embodiment 2

Figure 17:
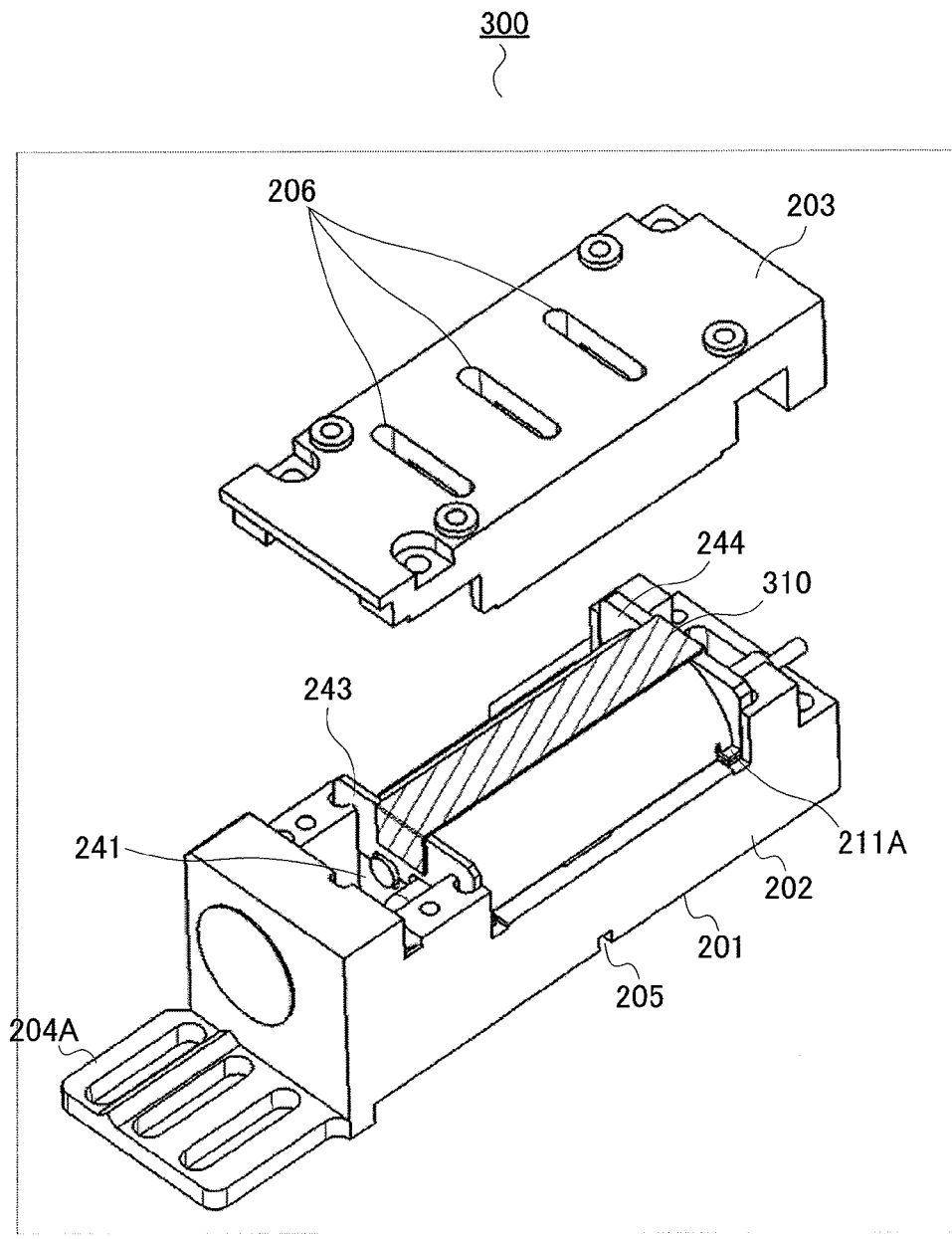
FIG. 17 is an exploded perspective view of a laser unit of a measurement device according to Embodiment 2 of the present invention.

FIG. 17 is an exploded perspective view of laser unit 300 of a measurement device according to Embodiment 2 of the present invention. For the description of the present embodiment, the same reference numerals are attached to the same elements in FIGS. 10 to 14 to omit a description of duplicate portions.

As shown in FIG. 17, in laser unit 300, heat transfer member 310 to connect support medium 243 and support medium 244 is mounted above upper lens-barrel 211.

Heat transfer member 310 is, for example, a copper foil tape. A wider copper foil tape is more advantageous in terms of thermal conduction performance.

Flash lamp 230 is supported by support media 241, 242, 243 and 244 (support members) having high thermal conductivity and support media 241, 242, 243 and 244 are in contact with lens-barrel 210. Further, heat transfer member 310 connects support medium 243 and support medium 244, and support media 243 and 244 and upper lens-barrel 211.

Heat generated by flash lamp 230 is transmitted to support media 241, 242, 243 and 244 in contact with flash lamp 230 and further, heat in support media 243 and 244 is dissipated by heat transfer member 310.

Heat dissipation via support media 243 and 244 can be performed on a wider surface and near vent hole 206 via heat transfer member 310. Accordingly, thermal conductivity can be increased so that heat dissipation performance can be improved. As a result, the effect of preventing thermal damage of hard glass tube 231 (see FIG. 15) constituting flash lamp 230 can further be enhanced.

Embodiment 3

Figure 18:
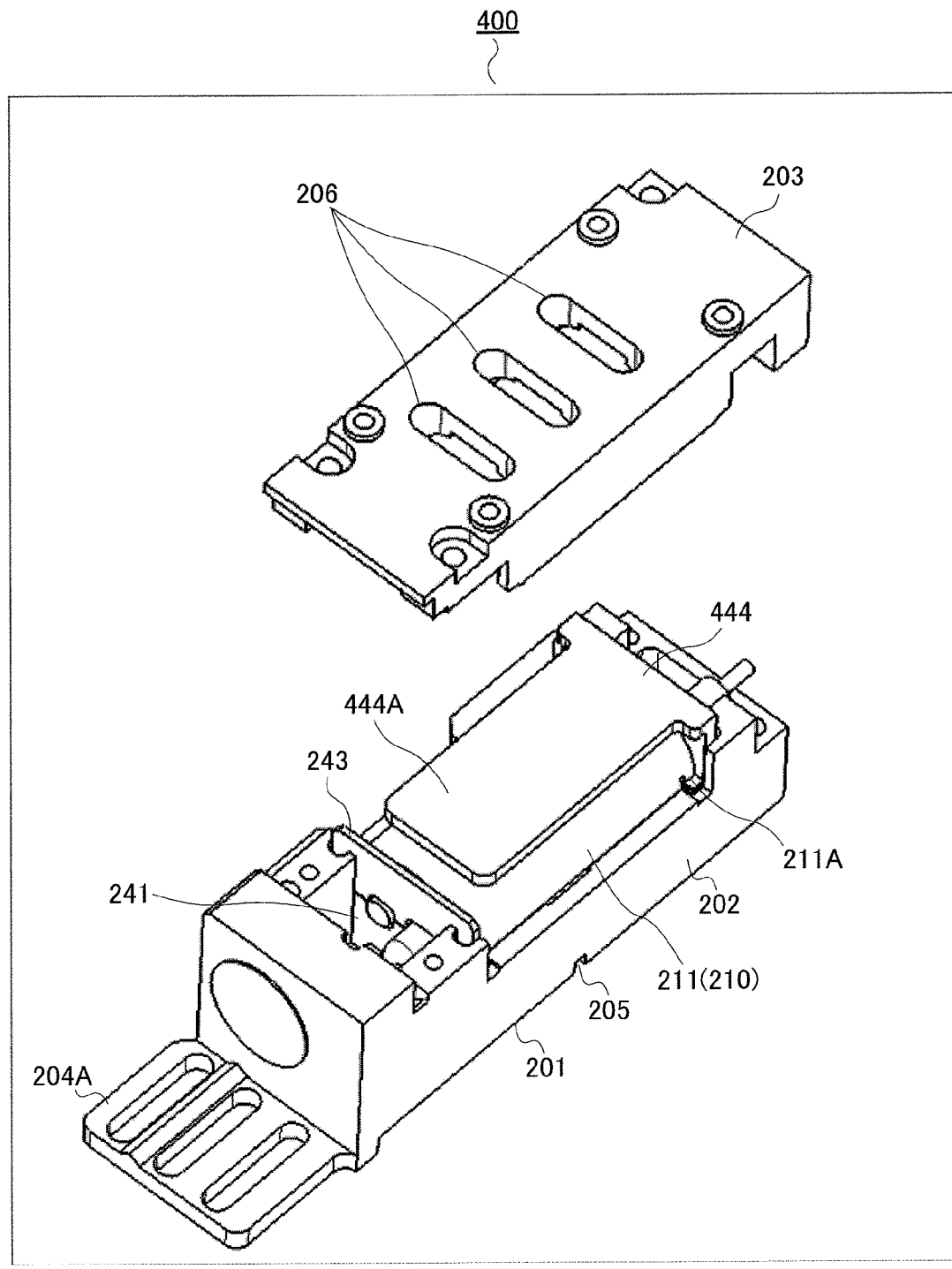
FIG. 18 is an exploded perspective view of a laser unit of a measurement device according to Embodiment 3 of the present invention.
Figure 19:
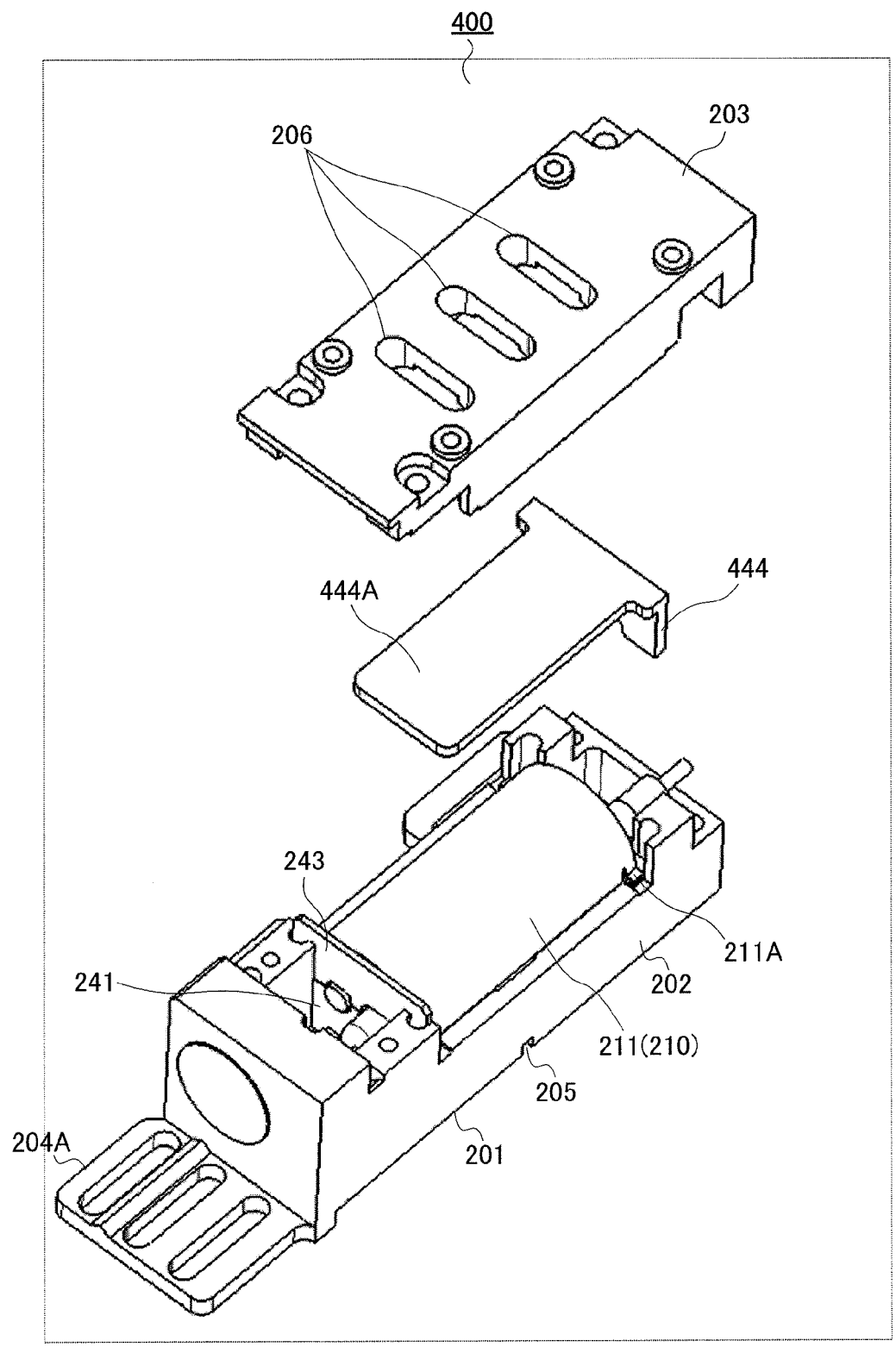
FIG. 19 is an exploded perspective view of the laser unit of the measurement device according to Embodiment 3.

FIGS. 18 and 19 are exploded perspective views of laser unit 400 of a measurement device according to Embodiment 3 of the present invention. For the description of the present embodiment, the same reference numerals are attached to the same elements in FIGS. 10 to 14 to omit a description of duplicate portions.

As shown in FIGS. 18 and 19, laser unit 400 includes, instead of support medium 244 of laser unit 200 shown in FIG. 10, support medium 444 having heat dissipation/diffusion section 444A.

Figure 20:
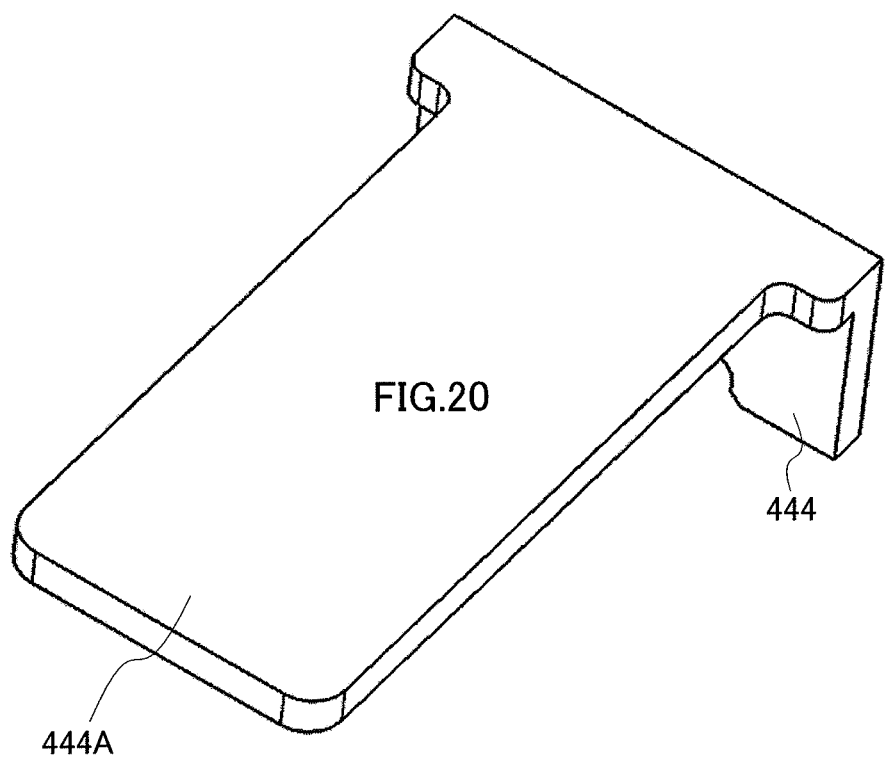
FIG. 20 is a perspective view showing a structure of a support medium of the laser unit of the measurement device according to Embodiment 3.

FIG. 20 is a perspective view showing the structure of support medium 444.

As shown in FIG. 20, support medium 444 has an L shape formed by integrating support medium 244 in FIG. 10 with heat dissipation/diffusion section 444A extending in the direction of the outer circumferential surface of lens-barrel 210.

Heat dissipation/diffusion section 444A is brought closer to the position of vent hole 206 of upper case 203 and extended in the direction of the outer circumferential surface of lens-barrel 210.

As described above, no laser light is emitted on the rear side of laser rod 220 and thus, the problem of dust adhesion is more tolerated than on the front side and a slight gap is allowed. Thus, a slight gap formed when heat dissipation/diffusion section 444A is formed by extending support medium 444 in an L shape causes no problem.

Heat dissipation via support medium 444 can be performed on a wider surface and near vent hole 206 via heat dissipation/diffusion section 444A. Particularly, heat can be dissipated directly from support medium 444 (support member), further improving heat dissipation performance. Accordingly, the effect of preventing thermal damage of hard glass tube 231 (see FIG. 15) constituting flash lamp 230 can further be enhanced.

Heat dissipation/diffusion section 444A may have any outer dimensions and shape. Heat dissipation/diffusion section 444A may have a slit and so on formed therein.

Heat transfer member 310 and/or heat dissipation/diffusion section 444A may be formed with the same material as support media 241, 242, 243 and 244 (support members).

The above description is an illustration of preferred embodiments of the present invention, but the scope of the present invention is not limited to the above illustration.

For example, the present invention may be applied to any apparatus that uses a laser emission apparatus as a puncturing means.

The name of the measurement device is used in each of the above embodiments, but this is for the sake of ease of explanation and the name may be a blood glucose level measurement device, puncturing unit or the like.

Each section constituting the measurement device, for example, the display section may adopt any type and the number and the connection method thereof are arbitrary.

The disclosure of Japanese Patent Application No. 2009-023460, filed on Feb. 4, 2009, including the specification, drawings and abstract, is incorporated herein by reference in its entirety.

INDUSTRIAL APPLICABILITY

A measurement device and a puncturing device according to the present invention represent a very important required technology to realize a blood glucose level measurement device equipped with a puncturing function of a laser puncturing method and a laser puncturing device. Widespread use of various measurement devices and puncturing devices is expected.

REFERENCE SIGNS LIST

100 Measurement device
200, 300, 400 Laser unit
202 Lower case
203 Upper case
204A, 204B Mounting section
201 Unit main body
205, 206 Vent hole
210 Lens-barrel
211 Upper lens-barrel
211A, 212A Leg section
212 Lower lens-barrel
220 Laser rod
230 Flash lamp
231 Hard glass tube
232 Positive electrode
233 Negative electrode
241, 242, 243 and 244, 444 Support medium (support member)
310 Heat transfer member
444A Heat dissipation/diffusion section

The invention claimed is:

1. A measurement device comprising a laser unit for puncturing, the laser unit including:
    a lens-barrel;
    a laser rod arranged inside the lens-barrel;
    a flash lamp arranged to oppose the laser rod inside the lens-barrel and having an inert gas sealed in a hard glass tube; and
    a support member at least a portion of which is arranged outside the lens-barrel and which supports an outer circumferential surface of the hard glass tube on a unit case and is made of a material having a thermal conductivity of 100 W/(m·K) or higher.

2. The measurement device according to claim 1, wherein the support member supports the outer circumferential surface of the hard glass tube in an outer circumference direction of an electrode inside the hard glass tube.

3. The measurement device according to claim 1, wherein the support members is arranged to block an opening of the lens-barrel.

4. The measurement device according to claim 1, wherein the support member is a pair of support media arranged such that openings at both ends of the lens-barrel are blocked.

5. The measurement device according to claim 1, wherein the support member is energized toward an opening of the lens-barrel.

6. The measurement device according to claim 1, wherein the support member includes a thermal diffusion section extending in a direction of the outer circumferential surface of the lens-barrel.

7. The measurement device according to claim 1, wherein the support member includes a heat transfer member to dissipate heat in the lens-barrel.

8. The measurement device according to claim 1, wherein the unit case has a vent hole provided in an outer circumference direction of the lens-barrel.

9. The measurement device according to claim 1, wherein a surface of the support member facing an opening of the lens-barrel is planished.

10. The measurement device according to claim 1, wherein the support member is formed with a metallic material.

11. The measurement device according to claim 1, wherein the support member is made of aluminum or an aluminum alloy.

12. A puncturing device that punctures a skin by radiating the skin with laser light by a laser unit, the laser unit comprising:
    a lens-barrel;
    a laser rod arranged inside the lens-barrel;
    a flash lamp arranged to oppose the laser rod inside the lens-barrel and having an inert gas sealed in a hard glass tube; and
    a support member at least a portion of which is arranged outside the lens-barrel and which supports an outer circumferential surface of the hard glass tube on a unit case and is made of a material having a thermal conductivity of 100 W/(m·K) or higher.

13. The puncturing device according to claim 12, wherein the support member supports the outer circumferential surface of the hard glass tube in an outer circumference direction of an electrode inside the hard glass tube.

14. The puncturing device according to claim 12, wherein the support member is arranged to block an opening of the lens-barrel.

15. The puncturing device according to claim 12, wherein the support member is a pair of support media arranged such that openings at both ends of the lens-barrel are blocked.

16. The puncturing device according to claim 12, wherein the support member is energized toward an opening of the lens-barrel.

17. The puncturing device according to claim 12, wherein the support member includes a thermal diffusion section extending in a direction of the outer circumferential surface of the lens-barrel.

18. The puncturing device according to claim 12, wherein the support member includes a heat transfer member to dissipate heat in the lens-barrel.

19. The puncturing device according to claim 12, wherein the unit case has a vent hole provided in an outer circumference direction of the lens-barrel.

20. The puncturing device according to claim 12, wherein a surface of the support member facing an opening of the lens-barrel is planished.

21. The puncturing device according to claim 12, wherein the support member is formed of a metallic material.

22. The puncturing device according to claim 12, wherein the support member is made of aluminum or an aluminum alloy.

* * * * *